US012584104B2

(12) United States Patent
Sivanandane et al.

(10) Patent No.: US 12,584,104 B2
(45) Date of Patent: Mar. 24, 2026

(54) OVARIAN FOLLICLE CELLS AND CONSTRUCTS FOR FERTILITY TREATMENT AND HORMONE REPLACEMENT THERAPY

(71) Applicant: Wake Forest University Health Sciences, Winston-Salem, NC (US)

(72) Inventors: Sittadjody Sivanandane, Winston-Salem, NC (US); Russel C. Sequeira, Advance, NC (US); John D. Jackson, Clemmons, NC (US); Anthony Atala, Winston-Salem, NC (US); James J. Yoo, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 1170 days.

(21) Appl. No.: 17/449,015

(22) Filed: Sep. 27, 2021

(65) Prior Publication Data

US 2022/0010270 A1    Jan. 13, 2022

Related U.S. Application Data

(63) Continuation-in-part of application No. PCT/US2020/025111, filed on Mar. 27, 2020.

(60) Provisional application No. 63/085,178, filed on Sep. 30, 2020, provisional application No. 62/826,394, filed on Mar. 29, 2019.

(51) Int. Cl.
C12N 5/075        (2010.01)

(52) U.S. Cl.
CPC ........ C12N 5/0609 (2013.01); C12N 2501/31 (2013.01); C12N 2506/04 (2013.01)

(58) Field of Classification Search
None
See application file for complete search history.

(56) References Cited

U.S. PATENT DOCUMENTS

| | | | |
|---|---|---|---|
| 4,391,909 A | 7/1983 | Lim | |
| 4,589,402 A | 5/1986 | Hodgen et al. | |
| 4,663,286 A | 5/1987 | Tsang et al. | |
| 4,725,579 A | 2/1988 | Jones et al. | |
| 5,084,350 A | 1/1992 | Chang et al. | |
| 5,227,298 A | 7/1993 | Weber et al. | |
| 5,380,536 A | 1/1995 | Hubbell et al. | |
| 5,573,934 A | 11/1996 | Hossainy et al. | |
| 5,578,314 A | 11/1996 | Cochrum et al. | |
| 5,693,514 A | 12/1997 | Dorian et al. | |
| 5,762,959 A | 6/1998 | Soon-Shiong et al. | |
| 5,801,033 A | 9/1998 | Hubbell et al. | |
| 5,846,530 A | 12/1998 | Soon-Shiong et al. | |
| 6,783,964 B2 | 8/2004 | Opara | |

| | | | |
|---|---|---|---|
| 9,283,251 B2 | 3/2016 | Opara et al. | |
| 2016/0166620 A1 | 6/2016 | Opara et al. | |
| 2016/0237402 A1 | 8/2016 | Tilly et al. | |

FOREIGN PATENT DOCUMENTS

| | | |
|---|---|---|
| WO | 8904366 A1 | 5/1989 |
| WO | 9220359 A1 | 11/1992 |

OTHER PUBLICATIONS

Devine et al. Frontiers in Bioscience 7, d1979-1898, Sep. 1, 2002 (Year: 2002).*

Zarate-Garcia et a. Scientific Reports 6:27991 | DOI: 10.1038/srep27991, 2016. pp. 1-9 (Year: 2016).*

MacDonald, Julie A. (correspondence); Woods, Dori C.; Tilly, Jonathan L. So Reproductive Sciences, (Mar. 2019) vol. 26, Supp. Supplement 1, pp. 384A. Abstract No. S-254. Meeting Info: 66th Annual Meeting of the Society for Reproductive Investigation, SRI 2019. Paris, France. Mar. 12, 2016-2019. (Year: 2019).*

International Search Report and Written Opinion corresponding to PCT/US2020/025111; dated Aug. 11, 2020 (12 pages).

Agarwal, Sanjay K., et al., "Leptin Antagonizes the Insulin-Like Growth Factor-I Augmentation of Steroidogenesis in Granulosa and Theca Cells of the Human Ovary", The Journal of Clinical Endocrinology & Metabolism 84(3), 1999, 1072-1076.

Feng, Chun-Wei , et al., "Control of mammalian germ cell entry into meiosis", Molecular and Cellular Endocrinology 382(1), 2014, 488-497.

Havelock, Jon C., et al., "Ovarian granulosa cell lines", Molecular and Cellular Endocrinology 288, 2004, 67-78.

Honda, Arata , et al., "Isolation, characterization, and in vitro and in vivo differentiation of putative thecal stem cells", PNAS 104(3), 2007, 12389-12394.

Jeon, Myung Jae , et al., "Engineering Functional Rat Ovarian Spheroids Using Granulosa and Theca Cells", Reproductive Sciences 28, 2021, 1697-1708.

Jeon, Myung Jae , et al., "Optimized culture system to maximize ovarian cell growth and functionality in vitro", Cell and Tissue Research 385, 2021, 161-171.

Khanna, Omaditya , et al., "Synthesis of multilayered alginate microcapsules for the sustained release of fibroblast growth factor-1", J. Biomed. Mater. Res. Part A: 95A(2), 2010, 632-640.

Le Bouffant, R. , et al., "Meiosis initiation in the human ovary requires intrinsic retinoic acid synthesis", Human Reproduction 25(10), 2010, 2579-2590.

(Continued)

*Primary Examiner* — Marcia S Noble

(74) *Attorney, Agent, or Firm* — Myers Bigel, P.A.

(57) ABSTRACT

A method of providing a culture of oogonia stem cells comprising oogonia stem cells is provided. The method may further include culturing the oogonia stem cells with granulosa and theca cells to differentiate the oogonia stem cells into oocytes. In some embodiments, the culturing comprises including the oogonia stem cells in an in vitro follicle construct or a microcapsule comprising said granulosa and theca cells. Further described herein is a method of forming a bioengineered follicle construct capable of releasing a mature oocyte. An in vitro fertilization method using the mature oocyte is also provided.

13 Claims, 13 Drawing Sheets

(56) References Cited

OTHER PUBLICATIONS

Liu, Te , et al., "Transplantation of ovarian granulosa-like cells derived from human induced pluripotent stem cells for the treatment of murine premature ovarian failure", Molecular Medicine reports 13(6), 2016, 5053-5058.

Martin, Jessica J., et al., "Implications and Current Limitations of Oogenesis from Female Germline or Oogonial Stem Cells in Adult Mammalian Ovaries", Cells 8(2):93, Jan. 16, 2019.

Sittadjody, Sivanandane , et al., "Regenerative Medicine Approaches in Bioengineering Female Reproductive Tissues", Reproductive Sciences 28, 2021, 1573-1595.

Varras, Michail , et al., "Marker of stem cells in human ovarian granulosa cells: is there a clinical significance in ART?", Journal of Ovarian Research 5(article No. 36), Jan. 11, 2012.

Wickenheisser, Jessica K., et al., "Human ovarian theca cells in culture", Trends in Endocrinology & Metabolism 17(2), 2006, 65-71.

Cox, et al., "Embryology, Ovarian Follicle Development", StatPearls [Internet]. Treasure Island (FL): StatPearls Publishing; Jan. 2025. Retrieved from: https://www.ncbi.nlm.nih.gov/books/NBK532300/ on Aug. 5, 2025 (4 pages).

Kerr, et al., "The dynamics of the primordial follicle reserve", Reproduction 146: 205-215, 2013.

* cited by examiner

ORGANOIDS WITH ALL 3 CELL TYPES
OSCs+GCs+TCs

100µm

SCHEMATIC OF NATIVE FOLLICLE

TC
GC
OC

EXPECTED ORGANIZATION OF ENGINEERED FOLLICLE

MATURE OOCYTE

2-CELL EMBRYO

4-CELL EMBRYO

OVARIAN FOLLICLE CELLS AND CONSTRUCTS FOR FERTILITY TREATMENT AND HORMONE REPLACEMENT THERAPY

CROSS-REFERENCE TO RELATED APPLICATIONS

This application is a continuation-in-part of International Patent Application No. PCT/US2020/025111, filed Mar. 27, 2020, which claims the benefit of U.S. Provisional Patent Application No. 62/826,394, filed Mar. 29, 2019. This application also claims the benefit of U.S. Provisional Patent Application No. 63/085,178, filed Sep. 30, 2020. The disclosures of each of these applications are hereby incorporated by reference in their entireties.

BACKGROUND

Loss of ovarian function leading to infertility and hormonal imbalance can be from natural causes (e.g., premature ovarian failure) or due to surgical removal of ovaries as a part of cancer treatment or other gynecological-related issues.

To overcome infertility issues due to loss of ovarian function, donor eggs (vitrified oocytes from a donor) are currently used in assisted reproductive techniques. It was previously believed that eggs (oocytes) are formed from their mother cells (oogonia) during the embryonic period, and all female babies are born with a definite set of pre-formed oocytes. This definite pool of pre-formed oocytes declines with age in addition to the monthly procurement of a few oocytes for maturation and ovulation. However, the recent discovery of oogonia stem cells (OSCs) from adult ovaries has opened a new avenue for maturing oocytes that could be used in assisted reproductive techniques, and various strategies have been employed in an effort to mature oocytes in vitro from oogonia stem cells obtained from adult ovary.

To address hormonal imbalance that may be caused by loss of ovarian function, administration of exogenous hormones (hormone replacement therapy, HRT) have been in use, but it is still controversial because of the adverse effect caused by the source, mode of delivery and control of delivery of such HRT. A cell-based hormone therapy (cHRT) using ovarian endocrine cells has also been described. See, e.g., U.S. Pat. No. 9,283,251 to Opara et al.

However, improved methods and compositions useful to treat a loss of ovarian function are needed.

SUMMARY

Provided herein is a method of providing a culture of oogonia stem cells, comprising: (a) providing a mixed population of ovarian cells isolated from an ovary tissue (e.g., adult human ovary tissue); (b) separating and collecting ovarian cells that are positive for: i) DEAD box helicase peptide 4 (DDX4, also known as Vasa homologue), and/or ii) interferon-induced transmembrane protein 3 (IFITM3, also known as fragilis), from said mixed population, to provide a double positive population of cells; and (c) culturing the double positive population of cells, wherein the double positive population of cells comprises oogonia stem cells.

In some embodiments, the separating is carried out with fluorescent-activated cell sorting (FASC), immunomagnetic bead sorting, or magnetic activated cell sorting (MASC).

In some embodiments, the providing step comprises: isolating ovarian cells from an ovary tissue; and culture expanding the ovarian cells in a germ-line stem cell media.

In some embodiments, the method further includes a step of collecting ovarian cells that are not positive for either DDX4 or IFITM3, to provide a second population comprising cells that can differentiate into granulosa and/or theca cells. In some embodiments, the method further comprises differentiating the cells of the second population into granulosa and/or theca cells.

In some embodiments, the method further includes culturing the oogonia stem cells with granulosa and theca cells (optionally produced as taught herein from cells not positive for either DDX4 or IFITM3), to differentiate the oogonia stem cells into oocytes. In some embodiments, the culturing comprises including the oogonia stem cells in an in vitro follicle construct or a microcapsule comprising said granulosa and theca cells. In some embodiments, the in vitro follicle construct or a microcapsule comprises an outer layer comprising the theca cells and an inner layer and/or core comprising the granulosa cells and the double positive population comprising oogonia stem cells. In some embodiments, the culturing includes contacting the oogonia stem cells with a combination of retinoic acid, follicle-stimulating hormone, and/or estradiol.

Also provided is an in vitro follicle construct comprising: live mammalian oogonia stem cells, or an oocyte differentiated from an oogonia stem cell (optionally wherein the oocyte is positive for DDX4 and DAZL); live mammalian granulosa cells; and live mammalian theca cells, optionally where the cells are provided in a hydrogel carrier (e.g., collagen hydrogel). In some embodiments the cells are provided in a cell culture apparatus such as a dish or plate.

In some embodiments, one, two, or all three of the live mammalian ovarian granulosa cells, live mammalian ovarian theca cells, and live mammalian oogonia stem cells are provided according to a method as described herein above and below.

In some embodiments, the construct is multilayered with the oogonia-stem cells in the center, the granulosa cells around them as a second layer, and the theca cells around the second layer as a third layer.

In some embodiments, the oogonia stem cells are included in the construct in an amount of from 500 cells to 5000 cells; the granulosa cells are included in the construct in an amount of from 1,000 cells to $1 \times 10^9$ cells; and/or the theca cells are included in the construct in an amount of from 1,000 cells to $1 \times 10^9$ cells.

Also provided is a method for performing in vitro fertilization, comprising: providing an in vitro follicle construct as taught herein, wherein the construct comprises the oocyte differentiated from the oogonia stem cells (optionally wherein the oocyte is positive for DDX4 and DAZL); collecting the oocyte; and fertilizing the oocyte, to thereby perform in vitro fertilization.

Further provided is a method of providing a culture of granulosa and/or theca cells, comprising one or more of the steps of: (a) providing a mixed population of ovarian cells isolated from an ovary tissue (e.g., adult human ovary tissue); (b) separating and collecting ovarian cells that are not positive for either: i) DEAD box helicase peptide 4 (DDX4, also known as Vasa homologue), or ii) interferon-induced transmembrane protein 3 (IFITM3, also known as fragilis), from said mixed population, to provide a population of sorted cells; (c) culturing the population of sorted cells; and (d) differentiating the sorted cells into granulosa and/or theca cells, wherein the granulosa cells are positive for FSH receptor and aromatase enzyme, and wherein the theca cells are positive for LH receptor and CYP17A1.

In some embodiments, the separating is carried out with fluorescent-activated cell sorting (FASC), immunomagnetic bead sorting, or magnetic activated cell sorting (MASC).

In some embodiments, the providing step comprises: isolating ovarian cells from an ovary tissue; and culture expanding the ovarian cells in a germ-line stem cell media.

In some embodiments, the method further includes forming an in vitro follicle construct or a microcapsule with the granulosa and/or theca cells, said microcapsule comprising: a core comprising live mammalian granulosa cells; and an auxiliary layer surrounding said core and comprising live mammalian theca cells.

Also provided herein according to some aspects of the present invention is an in vitro method for providing a three-layered bioengineered ovarian follicle. The method may include one or more of the steps: (a) providing a double positive population of cells, wherein said double positive population of cells comprises oogonia stem cells and are positive for: i) DEAD box helicase peptide 4 (DDX4, also known as Vasa homologue), and/or ii) interferon-induced transmembrane protein 3 (IFITM3, also known as fragilis); (b) inducing meiosis in the double positive population of cells (e.g., by culturing in a medium with all trans-retinoic acid (atRA)); then (c) adding granulosa cells to the cells and culturing the cells with follicle stimulating hormone (FSH); and then (d) adding theca cells and culturing the cells, to thereby provide the three-layered bioengineered ovarian follicle.

In some embodiments, the double positive population of cells are human cells.

In some embodiments, the double positive population of cells are produced by: (i) providing a mixed population of ovarian cells isolated from an ovary tissue; (ii) culture expanding the ovarian cells in a germ-line stem cell media to form an expanded population; and (iii) separating and collecting ovarian cells from the expanded population that are positive for said DDX4 and/or IFITM3.

In some embodiments, the separating is carried out with fluorescent-activated cell sorting (FASC), immunomagnetic bead sorting, or magnetic activated cell sorting (MASC).

In some embodiments, the method further comprises a step of collecting ovarian cells that are not positive for either DDX4 or IFITM3, to provide a second population comprising cells that can differentiate into granulosa and theca cells.

In some embodiments, the method further comprises differentiating the cells of the second population into granulosa and/or theca cells.

In some embodiments, the method further comprises the step of maturing the ovarian follicle by incubating the follicle in a medium comprising FSH for two to four weeks (e.g., about 18, 20, 21, 22, or 24 days).

In some embodiments, the method further comprises cyclical incubation of the ovarian follicle with (1) FSH; and (2) a combination of FSH and luteinizing hormone (LH), over period of from 10 or 12 to 16 or 18 days (e.g., about 14 days), and then exposing the ovarian follicle to a higher (e.g., 2, 3 or 4-fold) concentration of the LH in a combination of FSH and LH, whereupon an oocyte is released by the ovarian follicle.

In some embodiments, the oocyte released has a diameter of from about 25, 40, or 50 microns to about 70, 90, 100, 110 or 120 microns. In some embodiments, the oocyte released has a diameter of from about 70 microns to about 90, 100, 110 or 120 microns.

In some embodiments, the oocyte has cell surface expression of ZP3 and ZP2.

In some embodiments, the oocyte undergoes parthenogenesis upon stimulation with strontium chloride.

Also provided is a method for performing in vitro fertilization, comprising: providing the oocyte released from a bioengineered ovarian follicle as taught herein; and fertilizing the oocyte in vitro, to thereby perform in vitro fertilization. In some embodiments, the fertilizing is carried out by adding sperm cell(s) to the oocyte in vitro.

DETAILED DESCRIPTION

Figure 1:
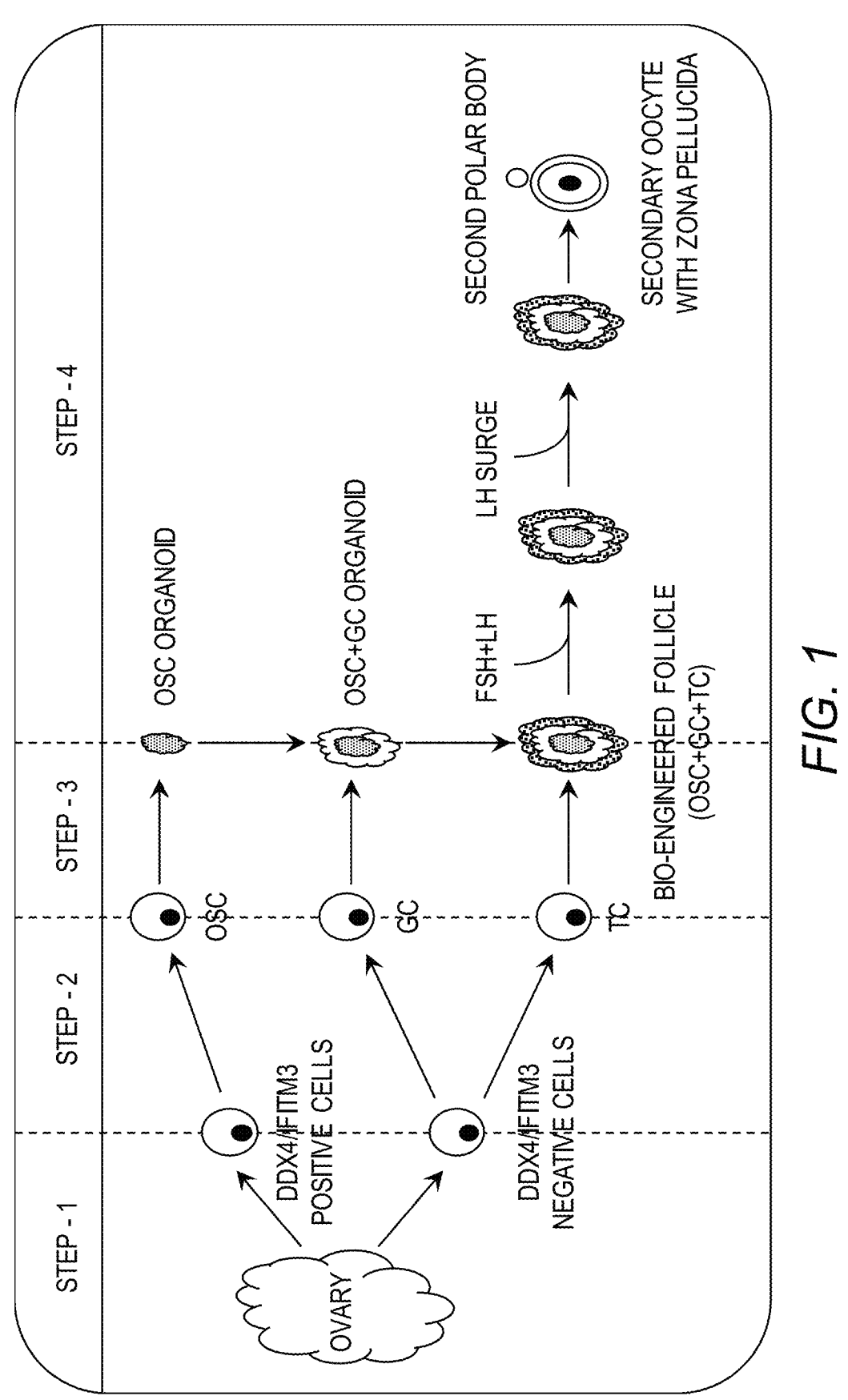
FIG. 1. Schematic of bio-engineered ovarian follicle formation. Briefly, egg progenitor cells or oogonia stem cells (OSCs) positive for DDX4 and/or IFTIM3 are isolated from the ovary. Isolated OSCs are expanded and characterized. Cells negative for these OSC markers are differentiated into somatic cells namely granulosa (GC) and theca (TC). During the bio-engineering of follicle process, first the OSCs are made into organoids, followed by the addition of GC and then finally TC. Bio-engineered follicles are exposed to follicle-stimulating hormone (FSH) and luteinizing hormone (LH) in a cyclic fashion followed by exposure to a LH surge. The production of secondary oocyte from the LH-surge exposed bio-engineered follicles is evaluated and characterized.

The disclosures of all United States patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" or "/" refers to and encompasses any and all possible combinations of one or more of the associated listed items, as well as the lack of combinations when interpreted in the alternative ("or").

"Subjects" as used herein are, in general, mammalian subjects. While human subjects are preferred, the subjects may in some embodiments be other animals, such as dogs and cats for veterinary purposes. Subjects are generally female. While the subjects may be of any suitable age, the subjects are typically adults.

"Treat" as used herein refers to any type of treatment that imparts a benefit to a subject, including but not limited to delaying the onset or reducing the severity of at least one symptom associated with hormonal imbalance or dysregulation in the subject, and/or promoting or enhancing fertility of the subject. For example, treating may be for infertility due to iatrogenic causes (especially patients treated with chemo/radiation) as well as naturally declining fertility with advancing age/menopause, to increase or enhance the reproductive lifespan of women who desire to have children later on in life with improved conception rates/viable pregnancies.

"Pharmaceutically acceptable" as used herein means that the microcapsule or composition is suitable for administration to a subject to achieve the treatments described herein, without unduly deleterious side effects in light of the severity of the disease and necessity of the treatment.

1. Ovarian Cells and Their Isolation

Cells used to carry out the present invention are, in general, live mammalian cells collected from a suitable donor. Donors are, in general, mammalian (e.g., human, dog, cat, rabbit, rat, mouse, monkey, chimpanzee, horse, pig, goat, sheep). The donor may be of the same species as the subject being treated, or of a different species. In some embodiments the donor may be the same subject undergoing treatment (i.e., autogenic), where suitable cells were harvested from the subject and provided as fresh tissue or stored for subsequent use (e.g., frozen).

Ovarian cells may be isolated from donors and cultured as taught herein or in accordance with techniques known in the art. See, e.g., Sanjay K. Agarwal et al., Leptin Antagonizes the Insulin-Like Growth Factor-I Augmentation of Steroidogenesis in Granulosa and Theca Cells of the Human Ovary, J. Clin Endocrinol Metab 84: 1072-1076 (1999); Jon C. Havelock et al., Ovarian granulosa cell lines, Molecular and Cellular Endocrinology 228, 67-78 (2004); Jessica K. Wickenheisser et al., Human ovarian theca cells in culture, Trends in Endocrinology & Metabolism 17, 65-71 (2006). In general, fresh tissue is divided by mincing, teasing, comminution and/or collagenase digestion. The desired cells are then isolated from contaminating cells and materials by washing, filtering, centrifuging or picking procedures, and optionally cultured and/or cryopreserved as desired prior to encapsulation.

The "primary culture" is the first culture to become established after seeding disaggregated cells or primary explants into a culture vessel. "Expanding" as used herein refers to an increase in number of viable cells. Expanding may be accomplished by, e.g., "growing" the cells through one or more cell cycles, wherein at least a portion of the cells divide to produce additional cells.

In some embodiments, the isolated ovarian cells are culture expanded. In some embodiments, the cells are cultured expanded in a germ line stem cell media supplemented with stem cell promoting growth factors. Such media may include ingredients such as, but not limited to, minimum essential medium alpha (αMEM), antibiotic/antimycotic (e.g., 1000 U/ml penicillin, 1000 μg/ml strep, 25 μg/ml amphotericin B), ITS (e.g., 5 mg/ml insulin, 5 mg/ml transferrin and 5 μg/ml selenium), glutamine (e.g., 2 mM), sodium pyruvate (e.g., 1 mM), nonessential amino-acids (e.g., 1 mM), fetal bovine serum (e.g., 10%), β-mercapto-ethanol (e.g., 0.1 mM), petrescine (e.g., 60 μM), epidermal growth factor (e.g., 10 ng/ml), basic fibroblast growth factor (e.g., 1 ng/ml), glial-derived neurotrophic factor (e.g., 40 ng/ml), leukemia-inhibitory factor (e.g., 10 ng/ml), insulin-like growth factor (e.g., 100 ng/ml), stem cell factor (e.g., 100 ng/ml), and combinations thereof, etc.

"Selecting", "sorting" or "separating" of cells can be performed based upon any unique properties that distinguish one cell type from another, e.g., density, size, unique markers, unique metabolic pathways, nutritional requirements, protein expression, protein excretion, etc. For example, cells may be selected based on density and size with the use of centrifugal gradients. Unique markers may be selected with fluorescent-activated cell sorting (FASC), immunomagnetic bead sorting, magnetic activated cell sorting (MASC), panning, etc. Unique metabolic pathways and nutritional requirements may be exploited by varying the makeup and/or quantity of nutritional ingredients of the medium on which cells are grown, particularly in a serum-free environment. Protein expression and/or excretion may be detected with various assays, e.g., ELISA.

In some embodiments, ovarian cells as taught herein may be selected/separated based on being positive for both of: i) DEAD box helicase peptide 4 (DDX4, also known as Vasa homologue), and ii) interferon-induced transmembrane protein 3 (IFITM3, also known as fragilis) (sometimes referred to herein as "double positive" population of cells in that the population is positive for both markers—i.e., contains cells positive for either or both of the markers). Such double positive cells may be differentiated into oogonia cells, and therefore are referred to as "oogonia stem cells." Ovarian cells that are not double positive may also be separated and collected for use, e.g., to provide granulosa and/or theca cells. Such markers may be used for separation with methods known in the art, such as with the use of marker-specific antibodies in fluorescent-activated cell sorting (FASC), immunomagnetic bead sorting, and/or magnetic activated cell sorting (MASC).

In some embodiments, ovarian stem cells (e.g., ovarian cells that are not positive for either DDX4 or IFITM3) may be stimulated into forming granulosa cells with a combination of different hormones and/or growth factors in a sequential fashion in accordance with procedures known in the art. The reagents, hormones and growth factors may include one or more of: all-trans retinoic acid, growth hormone, follicle-stimulating hormone, anti-müllerian hormone, β-estradiol, inhibin-α and -β, basic fibroblast growth factor, epidermal growth factor, and transforming growth factor-β. See Liu et al., 2016; Molecular Medicine reports 13:5053-5058. Similarly, ovarian stem cells (e.g., ovarian cells that are not double positive for DDX4 and IFITM3) may be differentiated into theca cells with a combination of various hormones and/or growth factors in accordance with procedures known in the art. The reagents, hormones and growth factors used for theca cell differentiation may include one or more of: Putrescine, D-(+)-glucose, Puyruvic acid, DL-Lactic acid, Ascorbic acid, 2-mercaptoethanol, D-biotin, epidermal growth factor, basic fibroblast growth factor, Glial cell-derived neurotrophic factor, insulin-like growth factor-I, stem cell factor, leukemia inhibitor factor, luteinizing hormone, β-estradiol and progesterone. See Honda et al., 2007; PNAS 104(30): 12389-12394.

In some embodiments, the oogonia stem cells may be stimulated to form oocytes with a combination of retinoic acid, follicle-stimulating hormone, and/or estradiol.

2. In Vitro Follicle Construct and Methods of Use for Fertility Treatment

The ovarian cells may be formed into an in vitro follicle construct including live mammalian oogonia stem cells, or an oocyte differentiated from an oogonia stem cell; live mammalian granulosa cells; and live mammalian theca cells. In some embodiments, the cells may be provided in a hydrogel carrier. The cells may be provided in a suitable cell culture apparatus such as a dish or plate (e.g., a 3D spheroid plate such as AggreWell™).

In some embodiments, the construct may be multilayered with the oogonia stem cells in the center, the granulosa cells around the oogonia stem cells as a second layer, and the theca cells around the second layer as a third layer. The construct/layers may or may not have cells encapsulated in one or more semipermeable membrane(s).

The in vitro follicle construct may be of any suitable size, such as from 10, 20 or 30 microns in diameter, up to 1000, 2000, or 5000 microns in diameter. The in vitro follicle construct may contain any suitable amount of cells. For example, in some embodiments, oogonia stem cells are included in the construct in an amount of from 500 cells to 5000 cells; granulosa cells are included in an amount of from 1,000 or 2,000 cells to $1\times10^6$, $1\times10^8$, or $1\times10^9$ cells; and theca cells are included in an amount of from 1,000 or 2,000 cells to $1\times10^6$, $1\times10^8$, or $1\times10^9$ cells. Mesenchymal stem cells, if present, may be included in the construct in any amount from 500 or 1000 cells to $0.5\times10^6$, to $0.5\times10^8$, $0.5\times10^9$, or $1\times10^9$ cells.

The in vitro follicle construct may be refrigerated and/or cryopreserved for subsequent use, and/or cultured for subsequent use, as desired.

In some embodiments, the oocyte is positive for DDX4 and DAZL (deleted in azoospermia like). See Varras, "Marker of stem cells in human ovarian granulosa cells: is there a clinical significance in ART?" Journal of Ovarian Research 5:36 (2012).

For fertility treatment, the formed oocyte may be collected from an in vitro follicle construct and fertilized by in vitro fertilization procedures. Methods for in vitro fertilization are known, and generally involve combination of an egg and sperm in vitro to form an embryo, which may then be implanted into a uterus of a subject. See, e.g., U.S. Pat. Nos. 4,589,402, 4,725,579, WO 1989/004366, WO 1992/020359.

3. Microcapsule Production and Methods of Use

In some embodiments, the cells are encapsulated to form a microcapsule. Encapsulation of live cells can be carried out in accordance with known techniques or variations thereof that will be apparent to those skilled in the art. See, e.g., U.S. Pat. No. 9,283,251 to Opara et al., the disclosures of which are incorporated by reference herein in their entirety. In some embodiments, the microcapsules contain theca and/or granulosa cells differentiated from ovarian stem cells as provided herein, and/or contain oogonia stem cells (or "double positive" cells) or oocytes differentiated therefrom.

Microcapsules useful in the present invention may optionally have at least one semipermeable membrane surrounding a cell-containing core and/or layer(s). The semipermeable membrane may permit the diffusion of nutrients, biologically active molecules and/or other selected products through the surface membrane and into the microcapsule core. The surface membrane contains pores of a size that determines the molecular weight cut-off of the membrane. The membrane pore size may be chosen to allow the passage of estrogen, and in some embodiments progesterone, from within the capsule to the external environment, but to exclude the entry of host immune response factors (where the administered microcapsules contain cells that are not autologous). Such a semipermeable membrane is typically formed from a polycation such as a polyamine (e.g., polylysine and/or polyornithine).

In one non-limiting example embodiment of an encapsulation technique, U.S. Pat. No. 4,391,909 to Lim et al. describes a method in which cells are suspended in sodium alginate in saline, and droplets containing cells are produced. Droplets of cell-containing alginate flow into calcium chloride in saline. The negatively charged alginate droplets bind calcium and form a calcium alginate gel. The microcapsules are washed in saline and incubated with poly-L-lysine or poly-L-ornithine (or combinations thereof); the positively charged poly-l-lysine and/or poly-L-ornithine displaces calcium ions and binds (ionic) negatively charged alginate, producing an outer poly-electrolyte semipermeable membrane. An exterior coating of sodium alginate may be added by washing the microcapsules with a solution of sodium alginate, which ionically bonds to the poly-L-lysine and/or poly-L-ornithine layer (this serves to reduce any inflammatory response that may be provoked in the subject by contact of the polycationic membrane to tissue). This technique produces what has been termed a "single-wall" microcapsule. A "double-wall" microcapsule can be produced by following the same procedure as for single-wall microcapsules, but prior to incubation with sodium citrate, the microcapsules are again incubated with poly-l-lysine and sodium alginate.

In additional non-limiting examples of encapsulation methods, Chang et al., U.S. Pat. No. 5,084,350 teaches microcapsules enclosed in a larger matrix, where the microcapsules are liquefied once the microcapsules are within the larger matrix. Tsang et al., U.S. Pat. No. 4,663,286 teaches encapsulation using an alginate polymer, where the gel layer is cross-linked with a polycationic polymer such as polylysine, and a second layer formed using a second polycationic polymer (such as polyornithine); the second layer can then be coated by alginate. U.S. Pat. No. 5,762,959 to Soon-Shiong et al. discloses a microcapsule having a solid (non-chelated) alginate gel core of a defined ratio of calcium/barium alginates, with polymer material in the core. U.S. Pat. Nos. 5,801,033 and 5,573,934 to Hubbell et al. describe alginate/polylysine microspheres having a final polymeric coating (e.g., polyethylene glycol (PEG)); Sawhney et al., Biomaterials 13:863 (1991) describe alginate/polylysine microcapsules incorporating a graft copolymer of poly-l-lysine and polyethylene oxide on the microcapsule surface, to improve biocompatibility; U.S. Pat. No. 5,380,536 describes microcapsules with an outermost layer of water soluble non-ionic polymers such as polyethylene(oxide). U.S. Pat. No. 5,227,298 to Weber et al. describes a method for providing a second alginate gel coating to cells already coated with polylysine alginate; both alginate coatings are stabilized with polylysine. U.S. Pat. No. 5,578,314 to Weber et al. provides a method for microencapsulation using multiple coatings of purified alginate. U.S. Pat. No. 5,693,514 to Dorian et al. reports the use of a non-fibrogenic alginate, where the outer surface of the alginate coating is reacted with alkaline earth metal cations comprising calcium ions and/or magnesium ions, to form an alkaline earth metal alginate coating. The outer surface of the alginate coating is not reacted with polylysine. U.S. Pat. No. 5,846,530 to Soon-Shiong describes microcapsules containing cells that have been individually coated with polymerizable alginate, or polymerizable polycations such as polylysine, prior to encapsulation.

When desired, the alginate-polylysine microcapsules can be incubated in sodium citrate to solubilize any calcium alginate that has not reacted with poly-l-lysine, i.e., to solubilize the internal core of sodium alginate containing the cells, thus producing a microcapsule with a liquefied cell-containing core portion. See Lim and Sun, Science 210:908 (1980). Such microcapsules are referred to herein as having "chelated", "hollow" or "liquid" cores.

When desired, the microcapsules may be treated or incubated with a physiologically acceptable salt such as sodium sulfate or like agents, in order to increase the durability of the microcapsule, while retaining or not unduly damaging the physiological responsiveness of the cells contained in the microcapsules. See, e.g., U.S. Pat. No. 6,783,964 to Opara.

Another method for the production of microcapsules is described in O. Khanna et al., Synthesis of multilayered alginate microcapsules for the sustained release of fibroblast growth factor-1 J. Biomed. Mater. Res. Part A: 95A: 632-640 (2010).

Microcapsules may be of any suitable size, such as from 10, 20 or 30 microns in diameter, up to 1000, 2000, or 5000 microns in diameter. Microcapsules may contain any suitable amount of cells. For example, in some embodiments, granulosa cells are included in the microcapsules in an amount of from 1,000 or 2,000 cells per microcapsule up to $1\times10^6$, $1\times10^8$, or $1\times10^9$ cells per microcapsule; and the theca cells are included in the microcapsules in an amount of from 1,000 or 2,000 cells per microcapsule up to $1\times10^6$, $1\times10^8$, or $1\times10^9$ cells per microcapsule. Mesenchymal stem cells, if present, may be included in said microcapsules in any amount from 500 or 1000 cells per microcapsule up to $0.5\times10^6$, to $0.5\times10^8$, $0.5\times10^9$, or $1\times10^9$ cells per microcapsule. See US 2016/0166620 to Opara et al.

Microcapsules of the present invention may be administered after production, refrigerated and/or cryopreserved for subsequent use, and/or cultured for subsequent use, as desired. Microcapsules of the invention may be washed (e.g., in sterile physiological saline solution) prior to formulation and/or administration, as needed depending upon their manner of production.

Microcapsules of the present invention may be administered for hormone therapy per se or formulated for administration by any suitable technique, such as by mixing with sterile physiological saline solution. The microcapsules may be administered by any suitable technique, including but not limited to surgical implantation or injection (either of which may be carried out subcutaneously, intraperitoneally, intramuscularly, or into any other suitable compartment, particularly into the omentum, such as by deposition into a surgically created omental pouch. Dosage of cells administered can be determined in accordance with known techniques or variations thereof that will be apparent to those skilled in the art.

Subjects or patients to be treated with hormone replacement therapy may include subjects afflicted with, or at increased risk of, one or more of osteoporosis, hot flashes, irregular period, vaginal atrophy, vaginal and/or bladder infection, incontinence (e.g., urge incontinence, stress incontinence), fatigue, sleep disturbances, irritability, mood swings, depression, loss of muscle mass, increased fat tissue, thinning and loss of skin elasticity, loss of bone tissue, impaired cognition etc., which may be associated with menopause, hysterectomy, ovariectomy, or other conditions for which estrogen or hormone replacement therapy is employed.

4. Maturation of Bioengineered Ovarian Follicle and Collection of Oocyte

Three-layered bio-engineered ovarian follicles formed by the methods taught herein may be matured by incubation in a suitable medium such as a germ-line stem cell (GSC) medium supplemented with follicle stimulating hormone (FSH) for several days, to three or four weeks (e.g., about one, two, three or four weeks) (with media replenishment as appropriate, such as once every three days). In some embodiments, the maturation is carried out by incubation for about 3 weeks, or about 18, 20, 21, 22, or 24 days.

After the in vitro maturation, the bio-engineered follicles may be exposed to cyclical levels of FSH and luteinizing hormone (LH) for 14 days. An example timeline of the in vitro maturation is provided in FIG. 14. In the cyclical gonadotropin (FSH and LH) treatment scheme, the bio-engineered follicles may be incubated, for example, with FSH (e.g., about 10 ng/ml) for about 12 hours, followed by the addition of LH (e.g., about 1 ng/ml) to the FSH-containing media, for incubation with a combination of FSH+LH for the next approximately 12 hours. This is repeated every day for a total period of from 10 or 12 to 15 or 16 days (e.g., 14 days).

At the end of the cyclical exposure to gonadotropin, an LH surge may be performed by incubating the bio-engineered follicles with the combination of FSH plus and excess of LH (e.g., 3-fold concentration of LH to that of the cyclic gonadotropin exposure). The oocytes released from the bio-engineered follicles after the LH surge may then be collected.

In some embodiments, the oocyte released has a diameter of from about 25, 40, or 50 microns to about 70, 90, 100, 110 or 120 microns. In some embodiments, the oocyte released has a diameter of from about 70 microns to about 90, 100, 110 or 120 microns.

In some embodiments, the oocytes express one or more of the markers (e.g., two or more, three or more, four or more, five or more, six, or all seven of): Oocyte-derived bone morphogenetic protein 15 (BMP15) (key regulator of follicular development); DDX4 (DEAD box protein-4, an ATP-dependent RNA helicase, germline (oocyte) specific marker); GDF-9 (Growth and differentiation factor 9, essential for oocyte-dependent development of ovarian follicles beyond the primary follicle stage); IFITM3 (interferon-induced transmembrane protein-3, also referred as fragilis, a germline specific marker similar to DDX4); NALP5 (a maternal oocyte protein, required for normal early embryogenesis); SCP3 (Synaptonemal complex protein 3, a marker for meiosis); and ZP3 (zona pellucida protein-3, a sperm binding receptor essential for fertilization).

In some embodiments, the oocyte has expression of sperm cell receptors ZP3 and ZP2. In some embodiments, the ZP3 and ZP2 are expressed on the surface of the oocyte.

In some embodiments, the oocyte can undergo parthenogenesis and form 2-cell and 4-cell stage embryos upon stimulation with strontium chloride. See Versieren et al., 2010 (Reproductive BioMedicine Online, 21: 769-775). For example, stimulation with strontium chloride may be performed by incubation of the oocyte with 10 mM SrCl$_2$ in culture medium supplemented with 2 μg/ml cytochalasin D for 4 hours, washed after the SrCl$_2$ treatment and transferred into oocyte culture medium. The ability to undergo parthenogenesis confirms that the oocyte is mature and capable of developing into an embryo upon in vitro fertilization.

The present invention is explained in greater detail in the following non-limiting Examples.

EXAMPLES

Example 1. Bio-Engineered Ovarian Follicle for Fertility Treatment and Hormone Replacement Therapy We developed an isolation procedure to obtain two different populations of stem cells from adult ovaries (fresh tissue or frozen tissue) using specific cellular markers. Oogonia stem cells (OSCs) are purified by the presence of two markers: a) DEAD box helicase peptide 4 (DDX4 also referred as Vasa homologue) and b) interferon-induced transmembrane protein 3 (IFITM3 also referred as fragilis). The double positive cells were characterized to be the OSCs, and stem cells that are negative for OSC markers were characterized to be stem cells from granulosa and theca cells.

A bio-fabrication process was developed to construct and mimic an ovarian follicular structure using three functional cell types of ovaries, namely: a) oocytes or oogonia; b) granulosa cells; and c) theca cells, which is schematically illustrated in FIG. 1.

A maturation system was developed to differentiate oocytes from their stem cells by incorporating them in ovarian follicle-like organoids, where granulosa and theca cells form the other components of the organoids. These somatic cells (granulosa and theca cells) induce the differentiation and maturation of oocytes from the OSCs.

This technology may be used for the treatment for infertility due to iatrogenic causes (especially patients treated with chemo/radiation) as well as naturally declining fertility with advancing age/menopause. This could increase or enhance the reproductive lifespan of women who desire to have children later on in life with improved conception rates/viable pregnancies.

In addition, this approach may serve as a source of HRT with correction of hormonal imbalance that responds to patient's natural hormone axis/pathway and delivers more controlled, steady physiologic doses compared to current methods of HRT.

A. Isolation and Expansion of Human Ovarian Cells

Ovaries: Whole ovary or partial ovary or biopsy samples of ovary (fresh or frozen tissue) can be used for isolating cells.

Human ovaries procured through The National Disease Research Interchange (NDRI) and International Institute for the Advancement of Medicine (IIAMS) within 24 hours after obtaining from donor (deceased donors) were shipped in supporting nutrient media (Dulbecco's Modified Eagles Media) in wet ice. Ovaries were disinfected using iodine solution followed by antibiotic Hank's balanced salt solution (HBSS) buffer. Ovarian cells were isolated from the disinfected ovaries and obtained by dissociating ovarian tissue by using enzymes.

The cells that form the integral part of ovarian follicle include: a) oocyte, b) granulosa and c) theca cells. Of these three major cell types, oocytes are the germ cells and the other two types are somatic cells that act as supporting cells. From our initial study with the procured ovaries, we have observed that the aforementioned ovarian cells do not exist in a differentiated form or as functional cells. Instead, they exist as stem cells in ovaries as reported by others and by us in our prior rat studies. Oogonia stem cells (OSCs) serve as the mother cell for the production of an oocyte (clinically referred to as egg cell), whereas, other stem cells in the ovary differentiate into granulosa and theca cells. These stem cells upon proper stimulation are capable of differentiating into these functional cells.

Oogonia stem cells may be isolated by one of the following methods: a) culturing the primary ovarian cells until they form distinct stem cell clusters; b) by magnetic activated cell sorting using oogonia stem cell markers; c) by fluorescent activated cell sorting using oogonia stem cell markers; or d) by culturing the cells scraped off from the surface of ovaries as ovarian surface epithelium cells. Granulosa and theca stem cells may be isolated by magnetic activated cell sorting or fluorescent activated cell sorting using pluripotent stem cell markers (OCT-4, Nanog, SSEA-4, SOX-2).

Approach-1: Isolating OSCs from the Cluster Forming Primary Ovarian Cells

Figure 2:
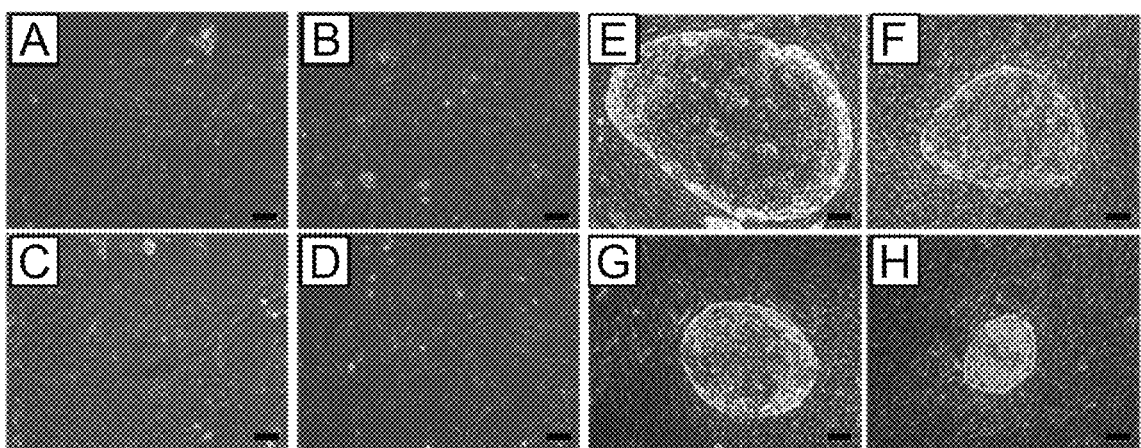
FIG. 2. Primary culture of ovary cells. Cells isolated from ovaries using enzymatic digestion were cultured in germ-line stem cell media (A-D). Some cells in the culture form distinct clusters on top of other cells (E-H). The scale bar in micrograph is 100 μm.

Even though the initial population of cells that are isolated from the ovaries yields a mixture of all kinds of ovarian cells, certain cell types aggregate and form clusters in the culture condition as shown in FIG. 2 (E-H). The primary cells isolated from ovaries were cultured in germ-line stem cell (GSC) media (minimum essential medium alpha ($\alpha$MEM) containing antibiotic/antimycotic (1000 U/ml penicillin, 1000 $\mu$g/ml strep, 25 $\mu$g/ml amphotericin B), ITS (5 mg/ml insulin, 5 mg/ml transferrin and 5 $\mu$g/ml selenium), 2 mM glutamine, 1 mM sodium pyruvate, 1 mM nonessential amino-acid, 10% fetal bovine serum, 0.1 mM $\beta$-mercaptoethanol, 60 $\mu$M petrescine, 10 ng/ml epidermal growth factor (Invitrogen), 1 ng/ml basic fibroblast growth factor, 40 ng/ml glial-derived neurotrophic factor, 10 ng/ml leukemia-inhibitory factor (LIF), 100 ng/ml insulin-like growth factor, 100 ng/ml Stem cell factor). In this culture condition (germ-line stem media supplemented with stem cell promoting growth factors), a particular population of cells formed aggregates. These clusters were carefully picked up and propagated further. After one generation of culture, the cluster forming cells were assessed for OSC markers.

Figure 3:
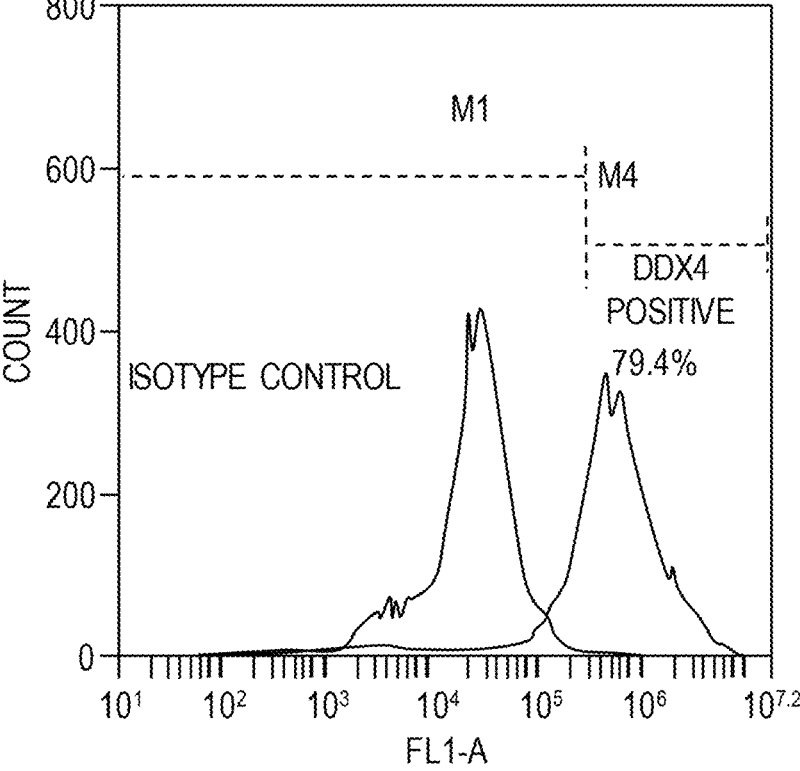
FIG. 3. Flow cytometry analysis. 79.4% of cluster forming cells are DDX4 positive.

OSCs are known to express a specific protein referred to as DEAD box polypeptide4 (DDX4), and this was used as a marker in our study to screen for OSCs in the cluster-forming cells. Briefly, the cells were incubated with antibody for DDX4 for 1 hr. Then, the cells were incubated with fluorescent-conjugated secondary antibody after washing of any unbound primary antibody. The cells were then analyzed by flow cytometry for the presence of fluorescent-labelled antibody complex. About 79.4% of cells were observed to be positive for the OSC marker (FIG. 3).

Figure 4:
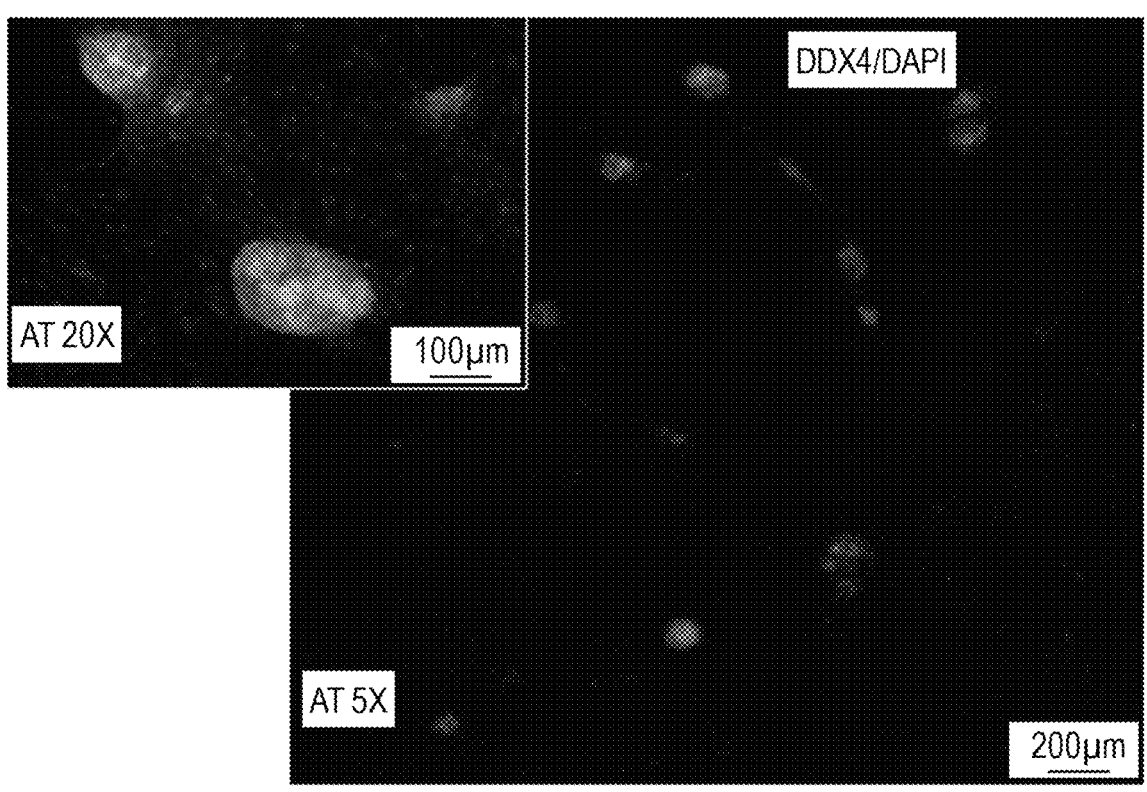
FIG. 4. Cluster forming cells stain for DDX4. Overall majority of the cells in the clusters are DDX4 positive.

In addition to flow cytometry analysis, the cluster forming cells in culture were also stained for DDX4 marker. As shown in the FIG. 4, a significant number of cells in the cluster stain positive for DDX4 validating flow cytometry data that a majority of the cluster forming cells are OSCs.

Approach-2: Enriching the Oogonia Stem Cells by a Magnetic Sorting Method

The two markers that were picked up from the immunofluorescent staining of ovary tissue, DDX4 and fragilis, were used to enrich the OSCs by magnetic sorting method from the cells isolated from ovaries. Briefly, the freshly isolated ovary cells were blocked for non-specific antibody binding for 30 min. Primary antibodies for DDX4 and fragilis were added and incubated for 45 min. After washing the unbound antibodies, magnetic bead conjugated secondary antibodies were added and incubated for 30 min. The cells were then passed through magnetic columns, where antibody-bound cells are separated from rest of the cells. Magnetically separated cells were washed and used for further studies. These enriched cells were characterized and propagated in vitro.

Figure 5:
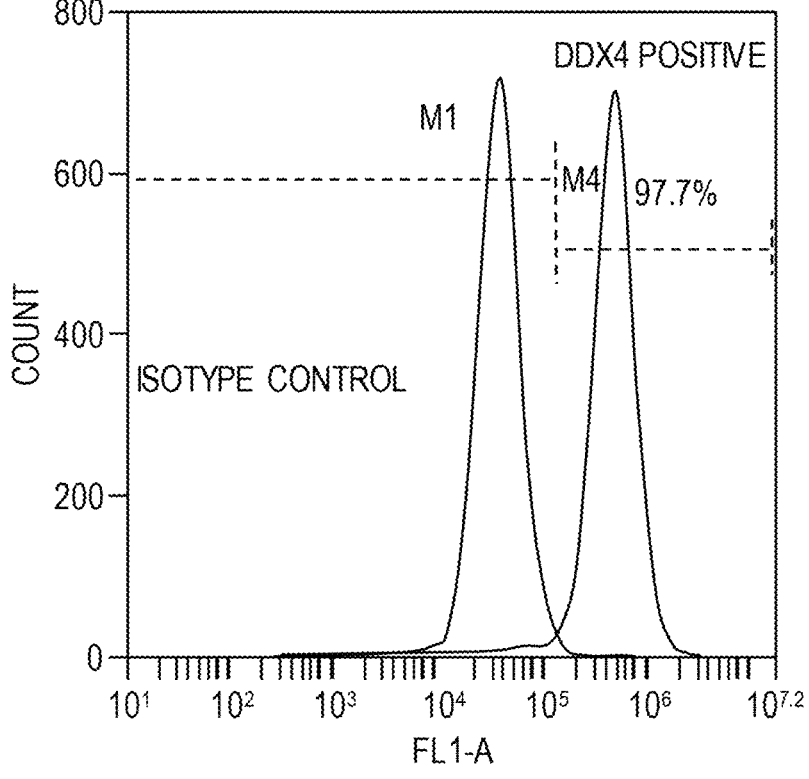
FIG. 5. Flow cytometry analysis. 97.7% of MACS-sorted cells are DDX4 positive, indicating that these cells maintain their stem cell properties in culture.

Similar to the cluster-forming cells, the MACS-sorted ovarian cells were expanded in culture and characterized. Immunofluorescent staining confirms the presence of OSCs in culture. With the help of flow cytometry, the percentage of OSCs among the cultured cells was assessed to determine how many cultured cells still carry their stem cell character after expansion. It was observed that about 98% of the MACS-sorted cells maintain their stem cell properties in culture (FIG. 5). Immunofluorescent staining for DDX4 and fragilis supported the flow cytometry data that the MACS-sorted cells in culture are OSCs (FIG. 6).

Approach-3: Expanding the Primary Ovarian Cells First and Then Enriching the OSCs by Magnetic Sorting Method Since the yield of the DDX4 and fragilis double positive population of cells from freshly isolated ovarian cells was very low (7.69%), we adopted an alternate method to increase the yield. In this modification, we cultured the ovarian cells that were isolated from the ovaries and expanded them in culture in the presence of germ-line stem cell media (minimum essential medium alpha ($\alpha$MEM) containing antibiotic/antimycotic (1000 U/ml penicillin, 1000 $\mu$g/ml strep, 25 $\mu$g/ml amphotericin B), ITS (5 mg/ml insulin, 5 mg/ml transferrin and 5 $\mu$g/ml selenium), 2 mM glutamine, 1 mM sodium pyruvate, 1 mM nonessential amino-acid, 10% fetal bovine serum, 0.1 mM $\beta$-mercaptoethanol, 60 $\mu$M petrescine, 10 ng/ml epidermal growth factor (Invitrogen), 1 ng/ml basic fibroblast growth factor, 40 ng/ml glial-derived neurotrophic factor, 10 ng/ml leukemia-inhibitory factor, 100 ng/ml insulin-like growth factor, 100 ng/ml stem cell factor). This allows the recovery of cells from the cold-ischemia and isolation-related shocks. In addition, the stem cells along with other cells increase in number. When these initially expanded cells were subjected to magnetic sorting for OSCs, the yield was found to be improved (30%). These initially expanded and MACS-sorted cells were cultured and characterized.

Figures 6, 7:
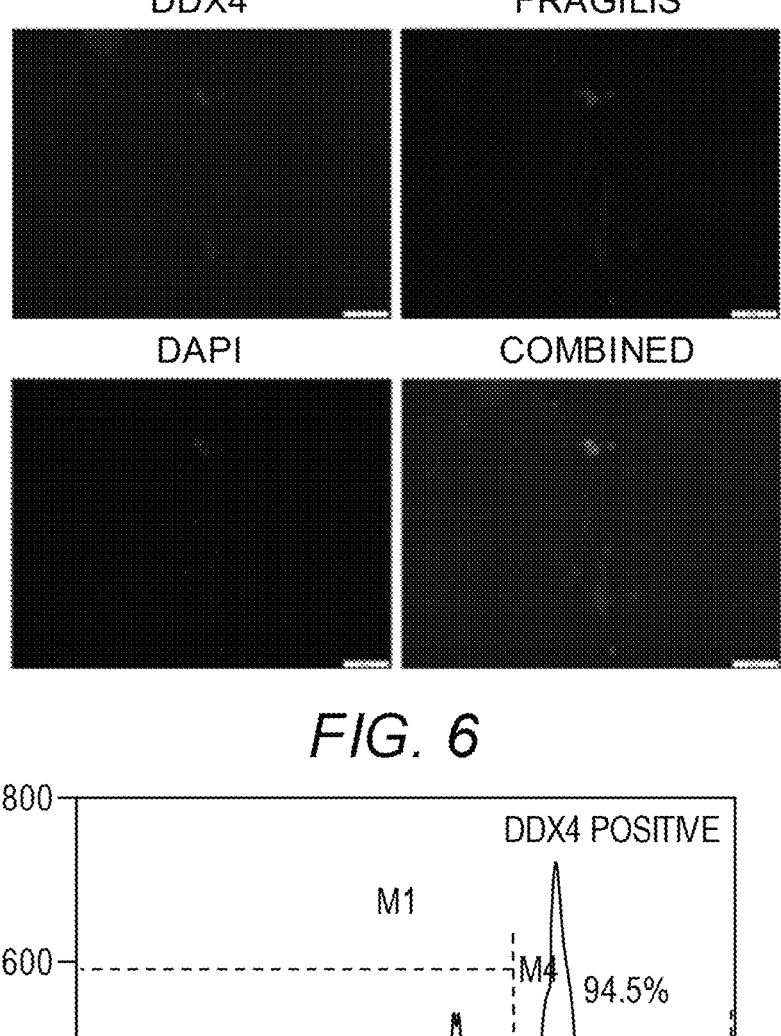
FIG. 6. Immunofluorescent staining of MACS-sorted cells. MACS sorted cells that are positive for DDX4 (a surface protein) maintain their stem cells properties in culture as shown by the immunofluorescent staining for DDX4 and Fragilis. The scale bar in the micrograph is 50 μm.
FIG. 7. Flow cytometry analysis. 94.5% of expanded and MACS-sorted cells are DDX4 positive.
Figure 8:
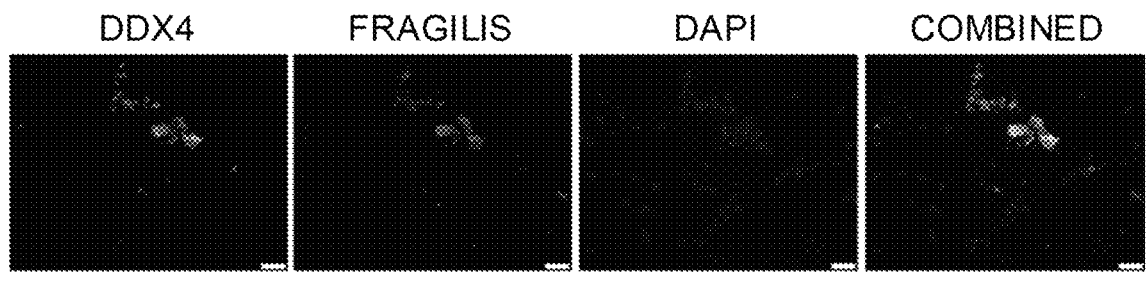
FIG. 8. Immunofluorescent staining of MACS-sorted cells from culture expanded ovarian cells. MACS sorted cells that are culture expanded before the magnetic sorting are positive for DDX4 (a surface protein), maintaining their stem cells properties in culture as shown by the immunofluorescent staining for DDX4 and Fragilis. The scale bar in the micrograph is 50 μm.

As a part of a characterization procedure, we have conducted both flow cytometry analysis for DDX4 positive cells and immunofluorescent staining for the OSC markers (FIG. 7 and FIG. 8). It was noted that this approach of initial expansion of primary ovarian cells and then enriching the OSCs has an advantage of improving the yield. Apart from that, the characteristics of the OSCs did not change by this modification.

B. Ovarian Stem Cells—Expansion and Differentiation

The stem cells isolated from the human ovary samples are heterogeneous. The three different cells of ovary that constitutes ovarian follicles (oocytes, granulosa and theca cells) are known to be derived from different stem cells. Cells isolated were expanded, characterized and used to fabricate into ovarian follicle-like structures. Ovarian stem cells are cultured and expanded by using appropriate stem cell media until they reach sufficient number ($1 \times 10^6$ to $1 \times 10^7$ cells) to differentiate them into respective functional ovarian cells.

Oogonia stem cells are cultured using germline stem cell media to maintain their stem-cell properties and to induce differentiation into oocytes. Granulosa cells (GC) and theca cells (TC) play a pivotal role in the maturation of oocytes. However, the availability of sufficient numbers of GCs and TCs from donor tissue (due to, for instance, the absence of many pre-existing follicle from the donors) can provide a challenge. Therefore, these two cell types were differentiated from the pluripotent stem cells of the ovary. Pluripotent stem cells are stimulated into granulosa cells with a combination of different hormones and growth factors in a sequential fashion. The reagents, hormones and growth factors include: all-trans retinoic acid, growth hormone, follicle-stimulating hormone, anti-mullerian hormone, β-estradiol, inhibin-α and -β, basic fibroblast growth factor, epidermal growth factor, and transforming growth factor-β. See Liu et al., 2016; Molecular Medicine reports 13:5053-5058. Similarly, pluripotent stem cells differentiate into theca cells with a combination of various hormones and growth factors. The reagents, hormones and growth factors used for theca cell differentiation include: Putrescine, D-(+)-glucose, Puyruvic acid, DL-Lactic acid, Ascorbic acid, 2-mercaptoethanol, D-biotin, epidermal growth factor, basic fibroblast growth factor, Glial cell-derived neurotrophic factor, insulin-like growth factor-I, stem cell factor, leukemia inhibitor factor, luteinizing hormone, β-estradiol and Progesterone. See Honda et al., 2007; PNAS 104(30): 12389-12394.

Figure 9:
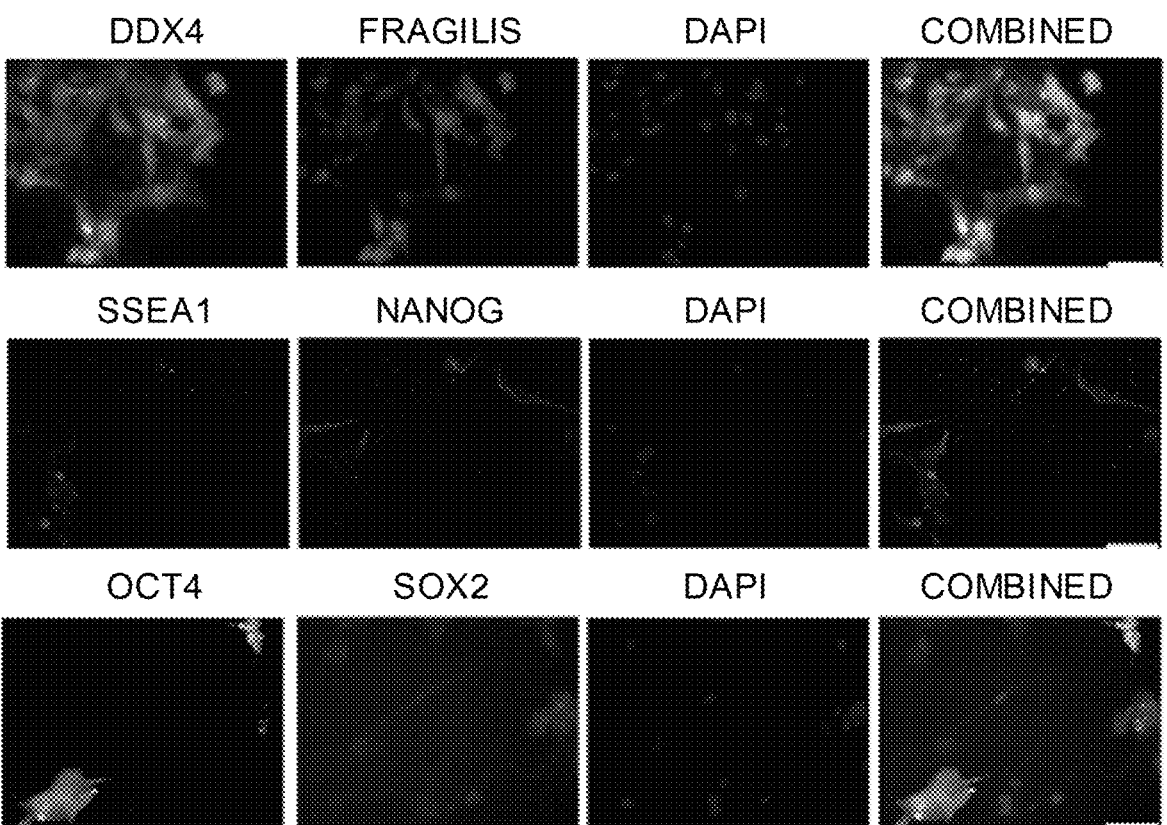
FIG. 9. Immunofluorescent staining of MACS-sorted ovarian cells in culture. Representative images of MACS-sorted ovarian cells in cultured stained for specific markers. Top row: DDX4 and IFITM3, the oogonia stem cell marker; Middle row: Nanog and SSEA1, pluripotent stem cell markers; and bottom row: OCT4 and SOX2, pluripotent stem cell markers. The scale bar in the micrograph is 50 μm.

During the long-term culture of OSCs, their stem cell characteristics were assessed to investigate how these cells maintain their stem cell properties in culture. During each passage cells were stained for markers that are specific for OSCs (DDX4 and IFITM3) and pluripotent stem cells (Nanog, SSEA1, OCT4 and SOX2). Percentage of cells for each marker was quantified from the images acquired from the immunofluorescent staining (FIG. 9) and analyzed semi-quantitatively.

Figure 10:
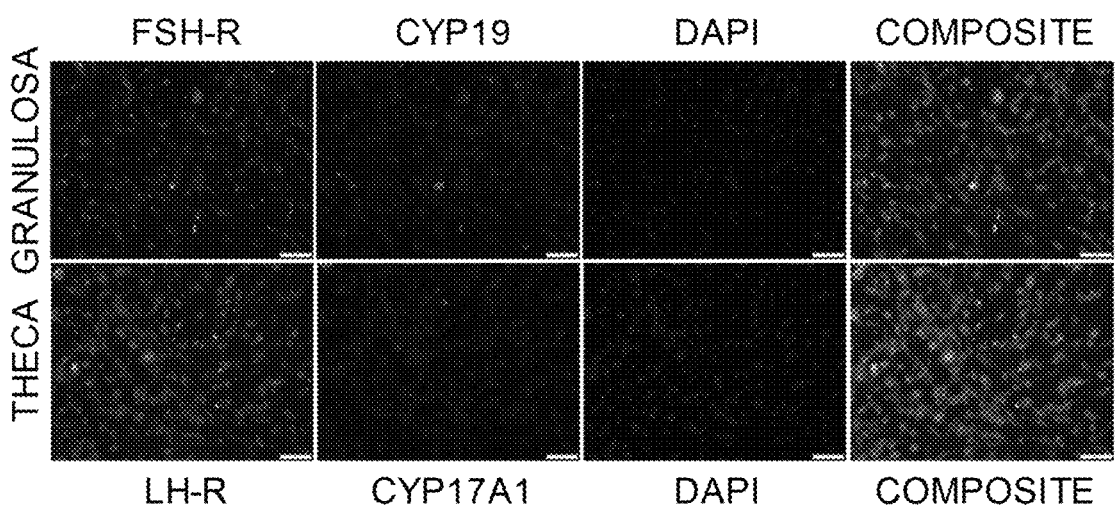
FIG. 10. Immunofluorescent staining of differentiated granulosa and theca cells. Representative images of differentiated granulosa and theca cells showing the expression of cell-specific markers. Top row: FSH receptor and aromatase (CYP19), the granulosa cell markers; bottom row: LH receptor and CYP17A1, theca cell markers. The scale bar in the micrograph is 50 μm.

Pluripotent stem cells that were treated with hormones and growth factors in their culture media differentiated into granulosa and theca cells. The differentiation into granulosa and theca cells was confirmed and characterized by the presence of cell-specific markers. Granulosa cells showed the expression of FSH receptor and aromatase enzyme, whereas theca cells exhibited the presence of LH receptor and CYP17A1, as shown in FIG. 10.

C. Bioengineering Human Follicle-Like Constructs

Oogonia-stem cells (OSCs) obtained from either cluster-forming cells in the primary culture of ovarian cells or from MACS/FACS sorting method was adopted to obtain OSCs using two specific markers which validate the reports from literature. In contrast to prior reports, however, we used both antibodies to select the cells to form a double positive population of cells, whereas other investigators have used only one antibody for selection. These isolated OSCs were then used for the construction of follicle-like organoids using an AggreWell™ system (STEMCELL Technologies Inc., Cambridge, Massachusetts). Once the cells formed organoids in AggreWell™ system, they were then transferred to 3 mg/ml collagen gel. After one week in collagen, the organoids were assessed histologically for the maturation of oocyte or oocyte-like cells.

Figure 11:
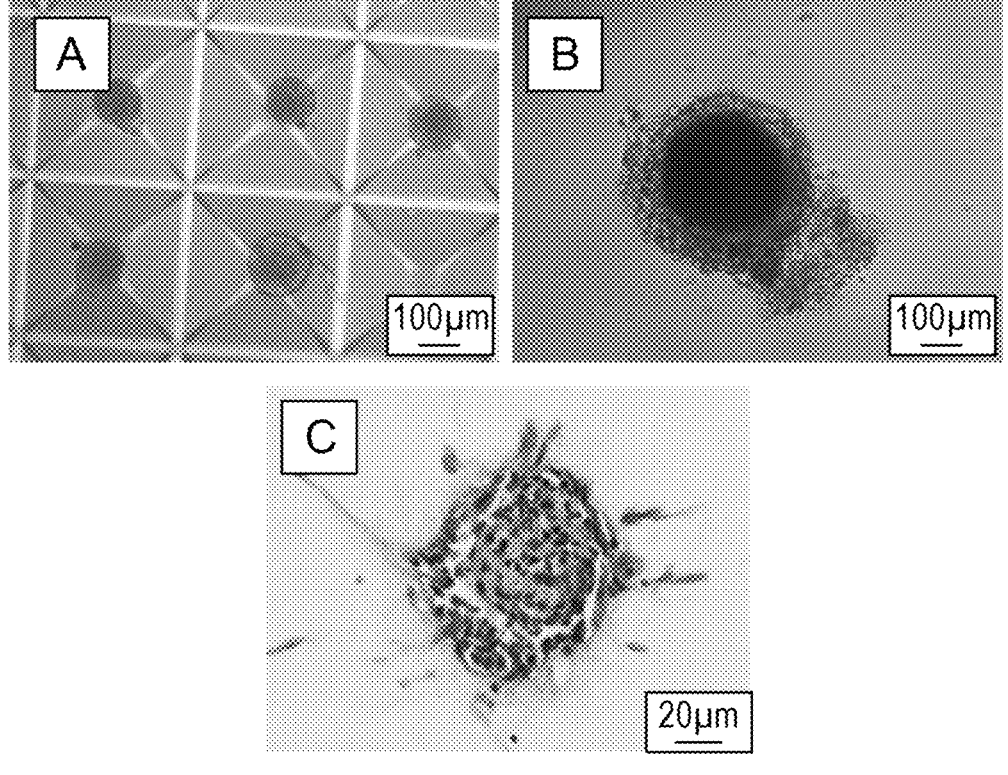
FIG. 11. Engineered organoids from Oogonia stem cells (OSCs). Panel A. Formation of ovarian cell organoids in AggreWell™ system; Panel B. Ovarian organoid harvested from collagen gel after one week of culture; Panel C. Histology of collagen gel-cultured ovarian cell organoid stained for hematoxylin and eosin. Scale bar for A and B=100 μm; for C=20 μm.

The organoids that were bio-engineered using the ovarian cells, when assessed for oocyte-like cell, showed no such visible oocyte-like cells. Even though the ovarian cells formed a follicle-like structure, they failed to produce any oocyte-like cells in culture (FIG. 11). Without wishing to be bound to any particular theory, this may have been due to a need for additional cues to be pushed into meiosis.

Example 2: Bio-Engineering Human Follicle-Like Ovarian Constructs Using OSCs, Granulosa (GCs) and Theca Cells (TCs) for In Vitro Oocyte Maturation In the engineering of follicle-like constructs, the OSCs were used along with the granulosa and theca cells. Each cell type is pre-stained with different fluorescent cell tracker dye in order to localize them in the engineered constructs. First, the pre-stained OSCs were used to make the core of the follicle-like construct. Once the formation of the core was confirmed, the second cell type granulosa were added to the construct and allowed to form second layer around the OSC core. Finally, the third cell type, theca cells, were added onto the periphery of the construct.

Figure 12:
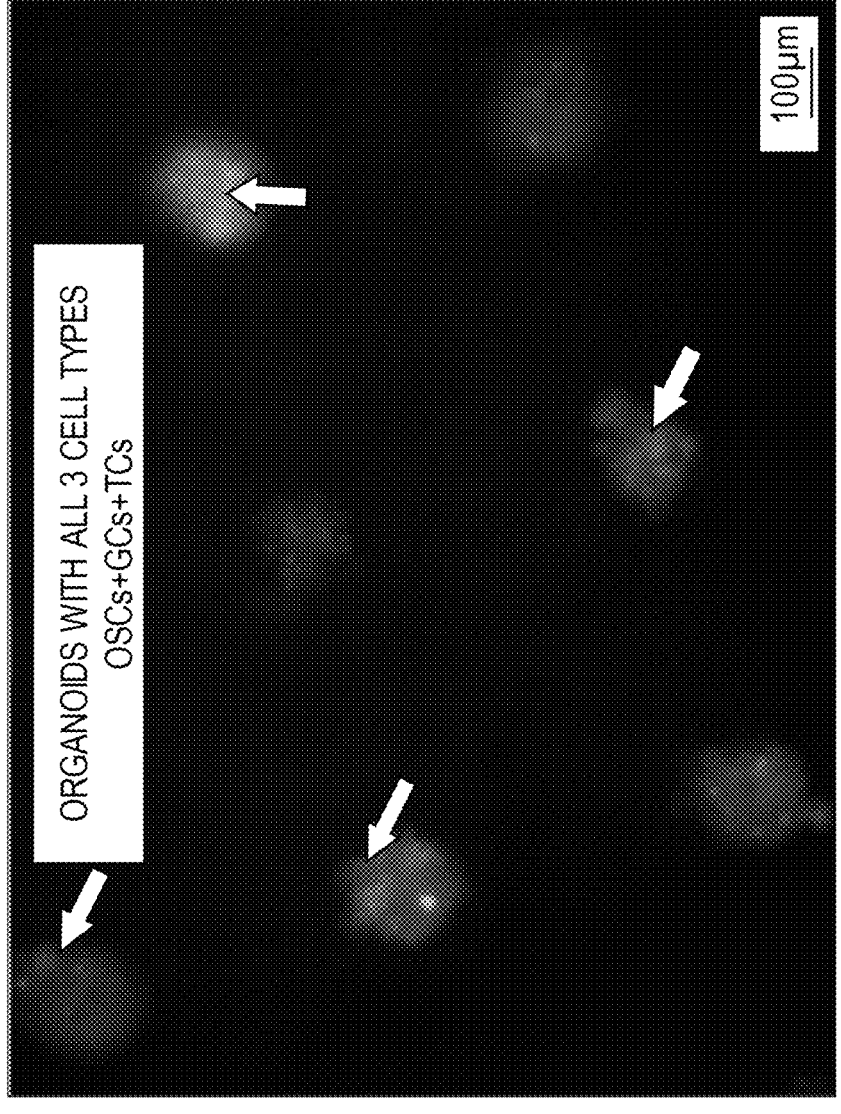
FIG. 12. Engineered organoids with three different cell types of ovarian follicles. The schematic of native follicle and expected organization of engineered follicle are provided on the left. Epi-fluorescent image of engineered follicle was provided on the right. OSCs were positioned in the core (indicated by arrow), granulosa cells layered around the OSC core and theca cells in the periphery. GC=granulosa cell; OSC=oogonia-stem cells; TC=theca cell.
Figure 12:
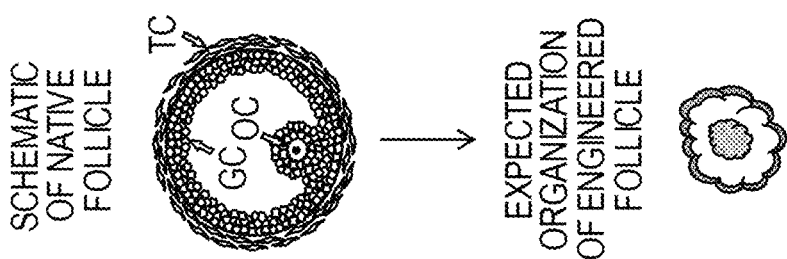

The epi-fluorescent image of an engineered human follicle made with this method is presented in FIG. 12 along with the schematic of native follicle and expected organization of engineered follicle. As evident from the figure, the engineered follicle formed a multilayered ovary organoid, with the oogonia-stem cells (OSCs) in the center, granulosa around them and theca as a final outer layer. It was also noted that OSCs in some of the organoids moved to periphery of the construct or were found off-centered (as indicated by the arrow).

Example 3: In Vitro Oogenesis from Laboratory-Engineered Ovary Organoids

The oogonia stem cells (OSCs) are mitotically diving cells, which need to enter meiosis to produce oocytes. Thus they may need special cues to push the mitotically dividing OSCs into meiosis. It has been reported in embryonic development where the oogonia cells are converted into primary oocytes, that one of the response factors of retinoic acid (RA), STRA8 increase during the transition of oogonia into oocyte (Le Bouffant et al., 2010, Human Reproduction 25(10): 2579-2590; Feng et al., 2014, Molecular and Cellular Endocrinology 382: 488-497), which may indicate a role of retinoic acid in this transition. We tested the combination of RA with other key hormones that a play vital role in oogenesis, namely follicle-stimulating hormone (FSH) and estradiol ($E_2$). RA in combination with FSH and E2 produced oocyte-like structures from the bio-fabricated ovary organoids in cultures.

Figure 13:
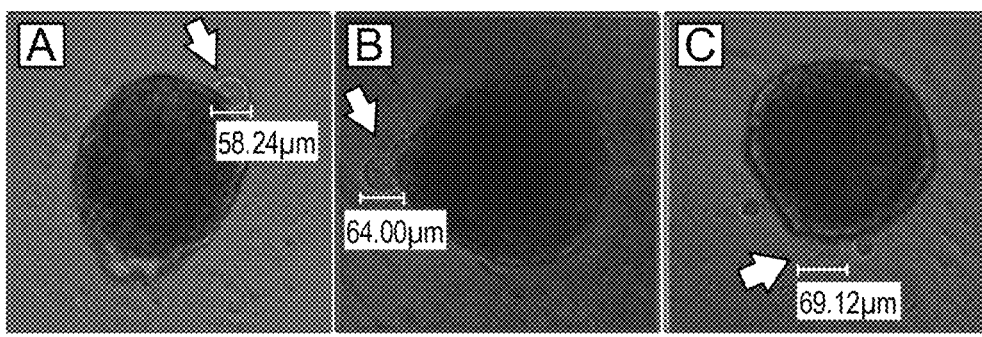
FIG. 13. In vitro oogenesis. Ovary organoids treated with the combination of retinoic acid (RA), follicle-stimulating hormones (FSH) and 17 β-estradiol (E2) for one week produced oocyte-like structures (Panels A-E, 10× magnification). These oocyte-like structures stain positive for DDX4 and DAZL, the markers of oocytes (Panels F-J, scale bar=20 μm).
Figure 13:
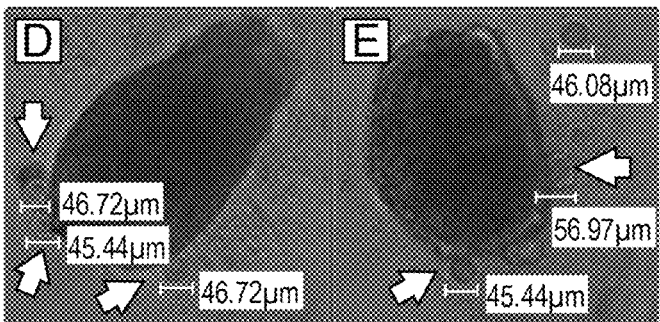
Figure 13:
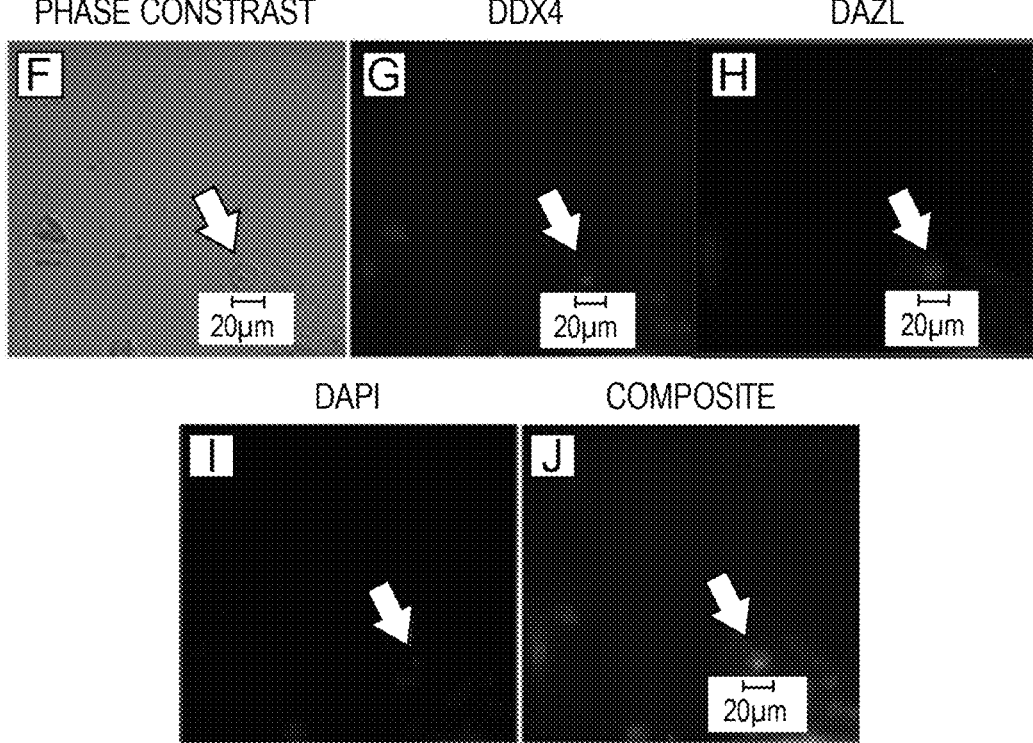

The laboratory-bioengineered ovary organoids produced oocyte-like structures that stained positive for early markers of oocytes, namely DDX4 and DAZL (FIG. 13). Further maturation of these oocyte-like structures will be carried out and characterized for late markers of oocytes.

Example 4: Stem Cell Selection for Somatic Cells and Egg Progenitors

First step is to isolate OSCs, the egg-progenitor cells and the stem cells for somatic cells from the donor human ovaries. Even though there are quite a few methods reported to isolate OSCs (including the use of surface markers), we chose to use surface marker-based cell sorting method. Since there are some concerns and controversies in the use of DDX4, we used an additional marker called Fragilis along with DDX4 thereby maximizing the yield of OSCs. In other words, the cells we isolate in our lab via magnetic sorting method could be positive for either DDX4 or Fragilis or both, to maximize our chance of obtaining more OSCs. The isolated OSCs are expanded and sub-cultured, as well as assessed for the maintenance of their stem cell characteristics.

Example 5: Somatic Cell Differentiation from Their Stem Cells and Bio-Engineering Ovarian Follicle Somatic cells like GCs and TCs are part of functional ovarian follicles (Follicles beyond the primary follicle stage, not primordial follicle stage); however, in human ovaries, the number of maturing follicles is very low. Therefore, these cells (GCs and TCs) are not available in the ovarian tissue from which OSCs are isolated. We used the remaining ovary cells after OSC isolation which contain somatic stem cells to differentiate into GCs and TCs. The differentiated cells were confirmed by immunofluorescence staining for respective markers of GCs and TCs. The expression of LH-receptor and CYP17 (cytochrome p450 17) are used as markers for TCs and the expression of FSH-receptor and CYP19 (aromatase enzyme) are used as markers for GCs.

In the bio-engineering process of ovarian follicles, the OSCs were made into an organoid by culturing them in an ultra-low attachment round-bottom culture plates. The OSC organoids were exposed to 1 µM retinoic acid (RA) in order to induce meiosis. The entry of meiosis was confirmed by immunofluorescence staining for an early marker of meiosis DAZL (deleted in azoospermia-like protein). This confirms the egg is at the primary oocyte stage. Then, the laboratory-differentiated GC, were added to the RA-primed OSC organoid as mentioned earlier, followed by the final addition of TC. This three cell type organoid mimics the structural architecture of an ovarian follicle. The follicle-like organoids are treated with exogenous pituitary gonadotropins in similar fashion that exists during the follicular phase in a reproductively active ovary. The gonadotropins-treated bio-engineered ovarian follicles produced sex steroids proving that a functional ovarian unit was produced. Apart from gonadotropins the culture media has been supplemented with other essential factors such as: EGF (10 ng/ml); FGF (10 ng/ml); GDNF (40 ng/ml); IGF-I (100 ng/ml); SCF or kit-ligand (100 ng/ml); BMP-4 (20 ng/ml); SDF (20 ng/ml); Forskolin (5 µM); N-Acetyl cysteine (1 mg/ml). These factors are included in the germline stem cells media as these factors are known to play an important role in the maturation of oocytes. The growth of primary oocyte-like structure were confirmed by measuring the size of the oocyte-like cells produced from the ovary organoids.

Example 6: In Vitro Oogenesis and Fertilizable Eggs

The final stage in the production of fertilizable eggs (secondary oocyte) is the completion of meiosis-I. As mentioned earlier, the somatic cells help in the maturation of primary oocytes; however, they hinder the progression of meiosis-I and completion by introducing a check point. The only way to relieve this check point is to luteinize the somatic cells by using high levels of LH, which is termed as a LH surge. Based on the literature, it has been estimated that the FSH level during LH surge is around 11 units/L, whereas the LH is 35 units/L, which is three times that of FSH level. Therefore, in our experiment we treated the follicle-like organoid with LH which was 3 fold higher than that of FSH, recapitulating the LH surge. Twenty-four to thirty-six hours after the LH surge, the ovary organoids are assessed for the production of secondary oocyte (fertilizable eggs) along with the first polar body.

Example 7: Bio-Fabrication of Human Ovarian Follicles and in Vitro Oogenesis OSCs were seeded onto the ultralow attachment 96 well plates and incubated overnight with GSC medium. GSC medium was then replaced with GSC medium without LIF and with all trans-retinoic acid (atRA) for 24 hours to induce meiosis. GCs were added to the atRA-treated OSC organoid and medium was replaced with GSC medium without LIF plus FSH for 48 hours. TC were added to the organoids composed of OSCs and GCs and incubated with GSC medium for the next 48 hours. The three-layered bio-engineered ovarian follicles was incubated with GSC medium with FSH for 21 days and the treatment media was replenished once in every three days during this in vitro maturation period.

Figure 14:
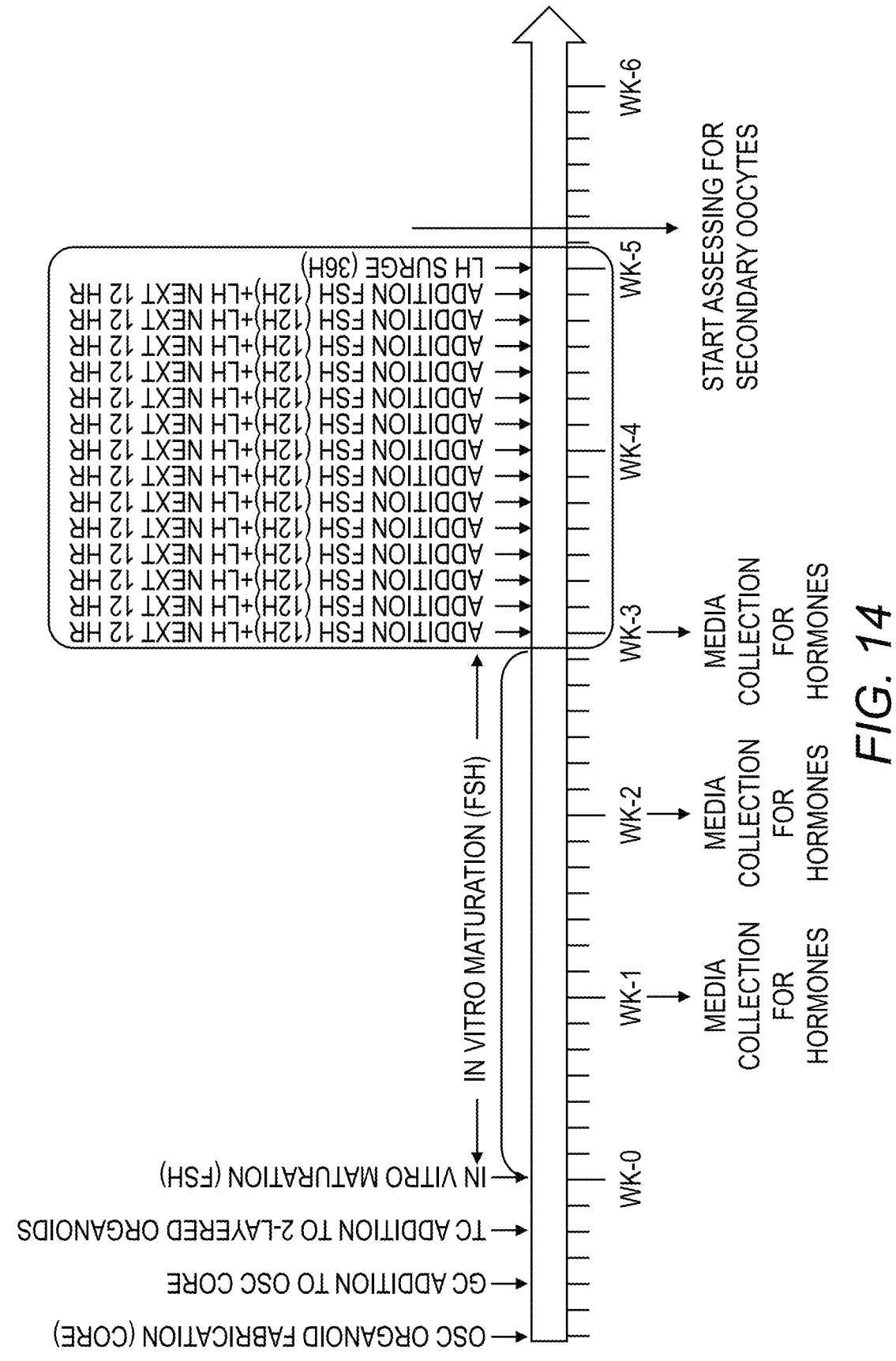
FIG. 14. Schematic of the bioengineering timeline. Bio-engineering of the human ovarian follicles is performed using OSCs, GCs and TCs; followed by the in vitro maturation of bio-engineered follicles by treating them with FSH for long-term; and finally inducing ovulation by introducing LH surge and assessing the quality of oocytes released from the bio-engineered follicles.

After three weeks of in vitro maturation, the bio-engineered follicles were exposed to cyclical levels of FSH and LH for 14 days, as illustrated in FIG. 14. In the cyclical gonadotropin (FSH and LH) treatment scheme, the bio-engineered follicles were incubated with 10 ng/ml FSH for 12 hours followed by the addition of 1 ng/ml LH to the FSH containing media yielding a combination of FSH+LH for the next 12 hours. The above-mentioned step is repeated every day for a total period of 14 days. At the end of 14 days cyclical exposure to gonadotropin, LH surge was introduced by incubating the bio-engineered follicles with combination 10 ng/ml FSH plus 30 ng/ml LH (3-fold concentration of LH to that of already existing FSH). Thirty-six hours after the induction of LH surge, the oocytes released from the bio-engineered follicles are collected and used for characterization and assessment of oocyte quality for fertilization competency and development competency.

Figure 15:
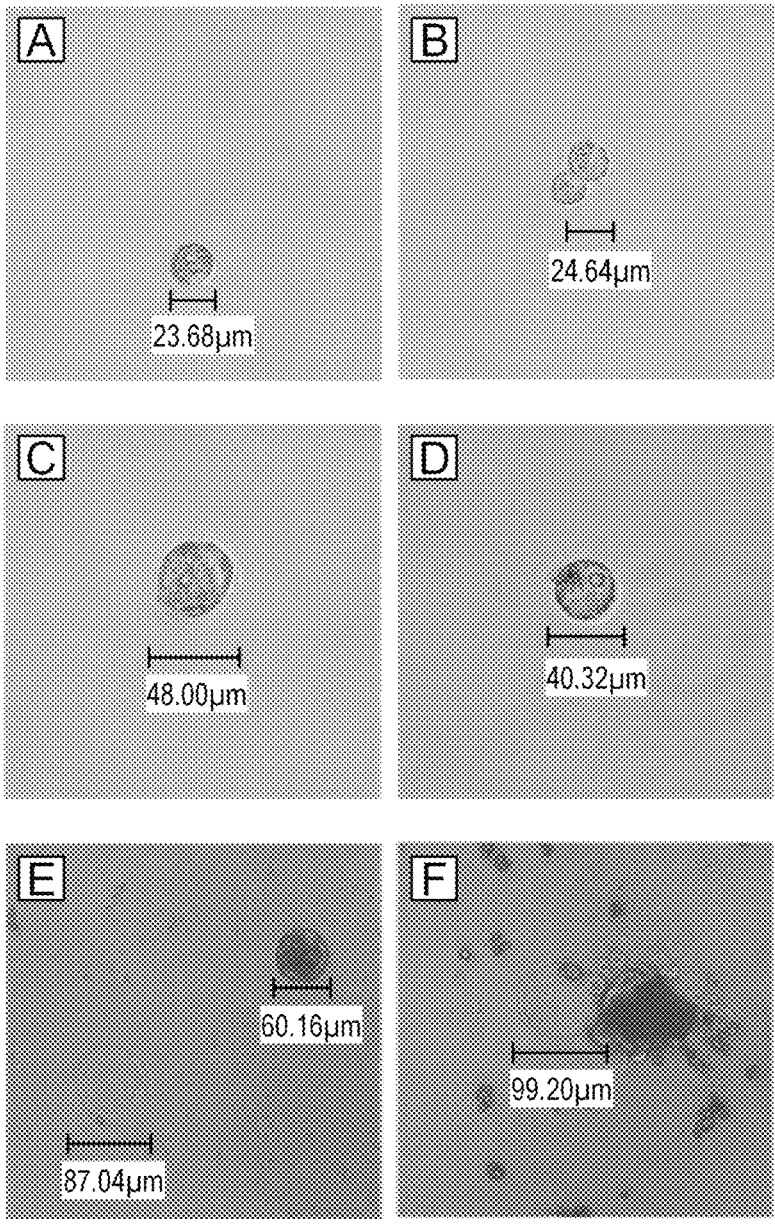
FIG. 15. Size of oocytes released from bio-engineered follicles. The oocytes released from the bio-engineered follicles were collected and visualized with an inverted microscope. The sizes of the oocytes were measured using imaging software. Sizes inclusive of about 24, 35, 40, 48, 90 and 100 microns were observed, as shown in Panels A-F.

Example 8: Assessing the Size of Oocytes Released from Bio-Engineered Follicles The oocytes released from the bio-engineered follicles were collected and visualized with an inverted microscope. The sizes of the oocytes were measured using imaging software. As shown in FIG. 15, sizes of about 24, 35, 40, 48, 90 and 100 microns were observed.

Example 9: Characterization of Oocytes for the Presence of Oocyte-Specific Markers The oocytes released from the bio-engineered follicles were collected and transferred onto a glass slide using a cyto-spinning procedure, followed by fixation, protein blocking and incubation overnight with primary antibodies for oocyte-specific markers. After washing the unbound primary antibodies, the slides with oocytes were incubated with fluorescent-conjugated secondary antibodies along with DAPI for 1 hour. After 1 hour, the unbound secondary antibodies and DAPI were washed off and imaged under microscope.

Figure 16:
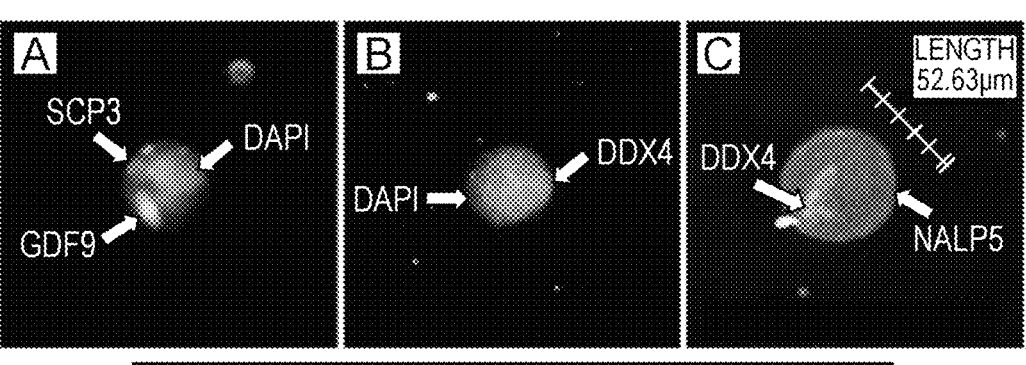
FIG. 16. Immuno-fluorescent staining of oocyte-specific markers. Immunofluorescent staining confirmed the presence of oocyte-specific markers in the oocytes released from the bio-engineered follicles: BMP15 (Oocyte-derived bone morphogenetic protein 15), DDX4 (DEAD box protein-4), GDF-9 (Growth and differentiation factor 9), IFITM3 (interferon-induced transmembrane protein-3), NALP5 (NACHT, LRR and PYD domains-containing protein 5), SCP3 (Synaptonemal complex protein 3), and ZP3 (zona pellucida protein-3), as shown in Panels A-K.
Figure 16:
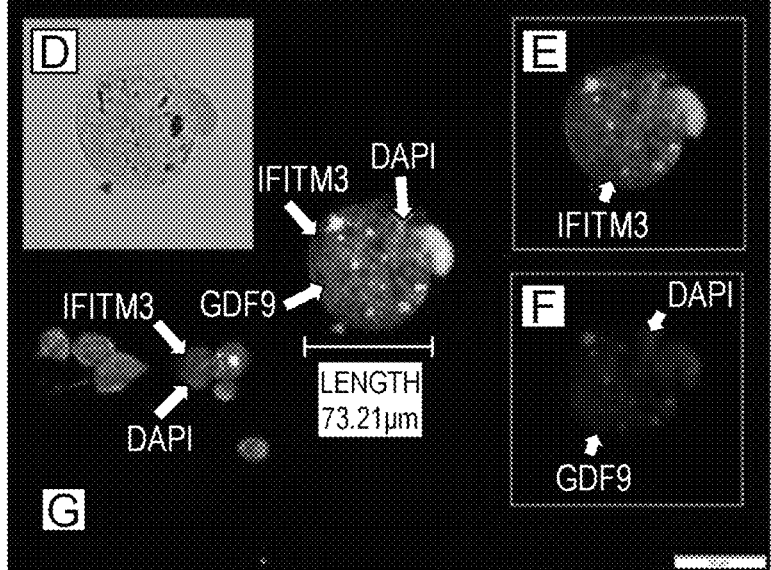
Figure 16:
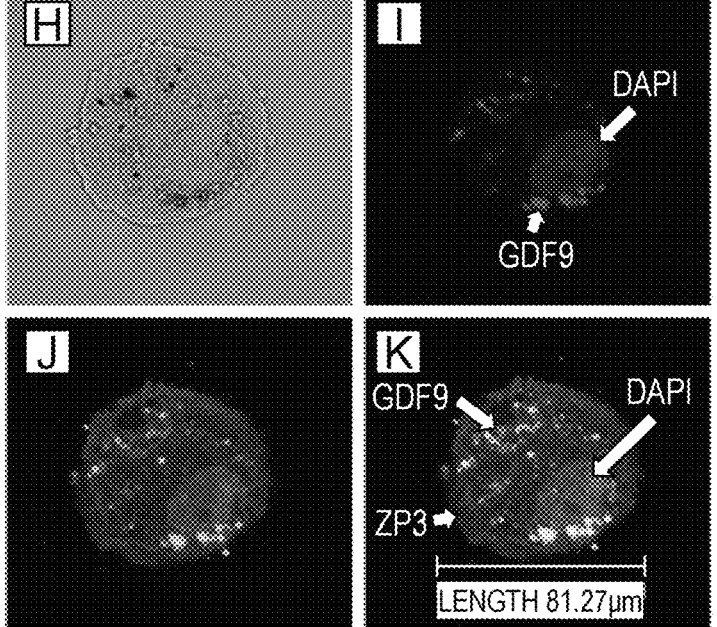

Immuno-fluorescent staining of oocyte-specific markers confirmed the presence of oocyte-specific markers in the oocytes released from the bio-engineered follicles, as shown in FIG. 16. Oocyte-derived bone morphogenetic protein 15 (BMP15) is key regulators of follicular development; DDX4 (DEAD box protein-4) is an ATP-dependent RNA helicase, germline (oocyte) specific marker; GDF-9 (Growth and differentiation factor 9) is essential for oocyte-dependent development of ovarian follicles beyond the primary follicle stage; IFITM3 (interferon-induced transmembrane protein-3) also referred as fragilis is a germline specific marker similar to DDX4; NALP5 (NACHT, LRR and PYD domains-containing protein 5) is a maternal oocyte protein, required for normal early embryogenesis; SCP3 (Synaptonemal complex protein 3) is a marker for meiosis; and ZP3 (zona pellucida protein-3) is a sperm binding receptor essential for fertilization.

The images show that the engineered oocytes express oocyte germ line markers such as DDX4 and IFITM3. In addition, the sperm binding protein ZP3 is expressed on the surface of the engineered oocyte.

Example 10: Evaluating the Fertilization Competency of the Oocytes Produced by Bio-Engineered Follicles The fertilization competency of the oocytes was assessed by the presence of two sperm receptors, namely ZP3 and ZP2. ZP3 is a glycoprotein present on the surface of zona pellucida and known to bind with sperm and induce acrosomal activation. Similarly, ZP2 is another glycoprotein present inside the zona pellucida on the surface of oocyte's plasma membrane, which binds to sperm head after the penetration process. Briefly, the oocytes collected from the bio-engineered follicles were transferred to a glass slide by cyto-spinning method followed by immune-fluorescent staining for the above-mentioned two sperm receptors.

Figure 17A:
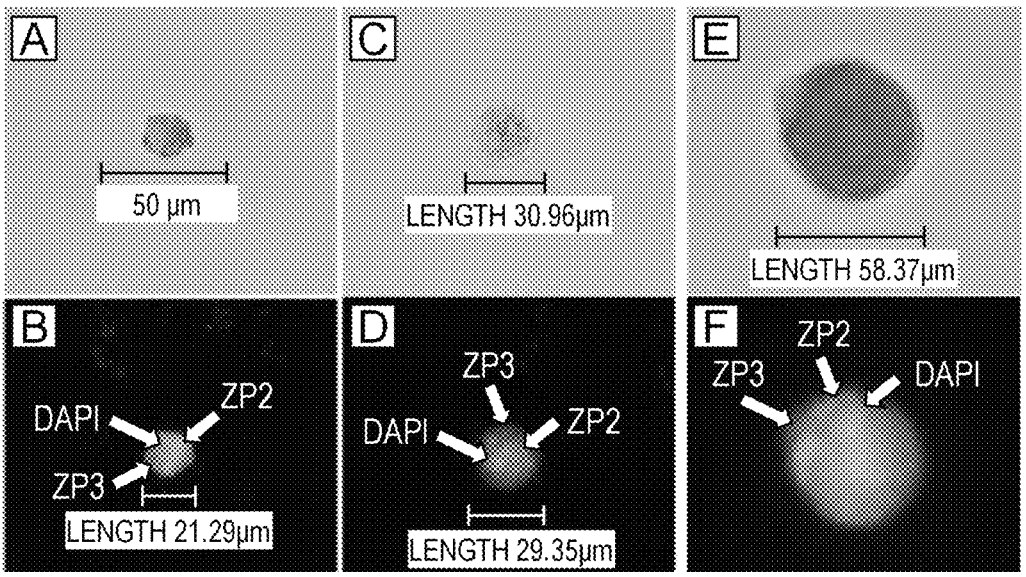
FIGS. 17A-17B. Presence of sperm receptors on engineered oocytes. Oocytes collected from the bio-engineered follicles were transferred to a glass slide by cyto-spinning method followed by immune-fluorescent staining for two sperm receptors: ZP3 and ZP2. Both sperm receptors were found in oocytes of different sizes, as shown in Panels A-F of FIG. 17A and Panels A-F of FIG. 17B.
Figure 17B:
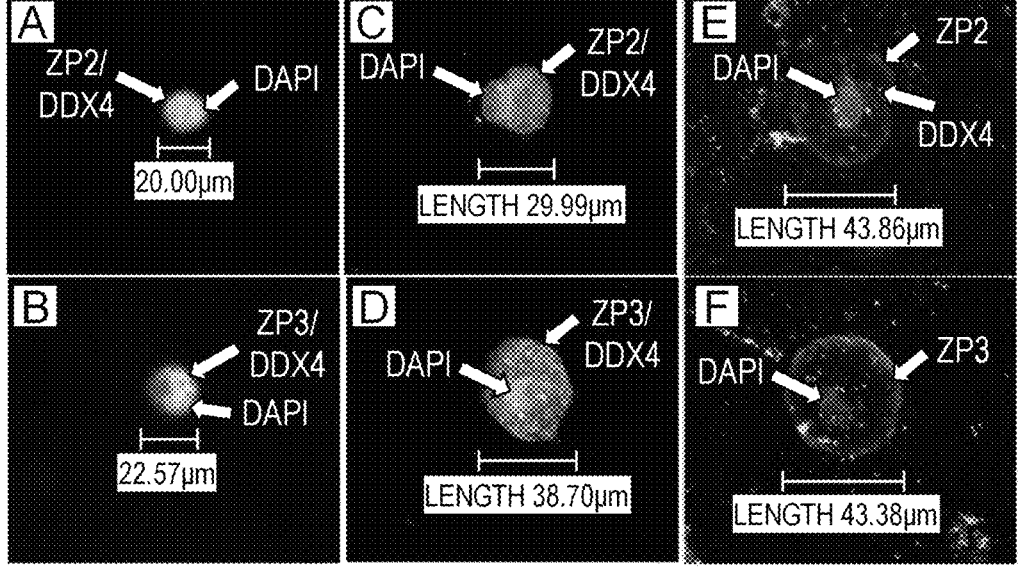

As shown in FIG. 17A and FIG. 17B, the engineered oocytes express both sperm binding proteins ZP3 and ZP2. This indicates that the oocytes have the potential to bind sperm, which is the initial and essential step in fertilization.

In addition, DDX4 is localized in the cytoplasm of the smaller oocytes. As the oocytes matures and increases in size, the location of DDX4 changes to the nucleus.

Example 11: Validating the Development Competency of the Oocytes Produced by Bio-Engineered Follicles The development competency of the oocytes was validated by inducing parthenogenesis and assessing the formation of early stage embryos (2-cell stage and 4-cell stage embryos). The collected oocytes from the bio-engineered follicles were cultured until they reach above 90 μm. Parthenogenesis was induced using strontium chloride ($SrCl_2$) as described in Versieren et al., 2010 (Reproductive Bio-Medicine Online, 21: 769-775). Briefly, the mature were incubated with 10 mM $SrCl_2$ in culture medium supplemented with 2 μg/ml cytochalasin D for 4 hours, washed after the $SrCl_2$ treatment and transferred into oocyte culture medium. The division of parthenogenesis-induced oocyte was assessed for presence of early stage embryos.

Figure 18:
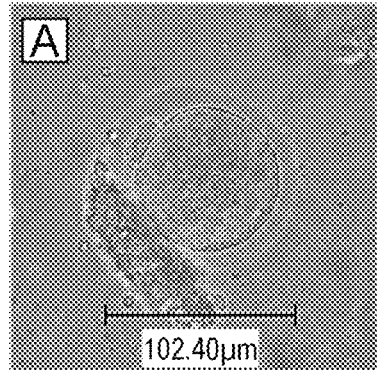
FIG. 18. Bioengineered oocyte parthenogenesis. The mature oocyte obtained from the bioengineered follicles, when induced with strontium chloride to undergo the parthenogenesis process, divided into a two cell-stage and then into a four cell-stage embryo in vitro, validating their development competency.
Figure 18:
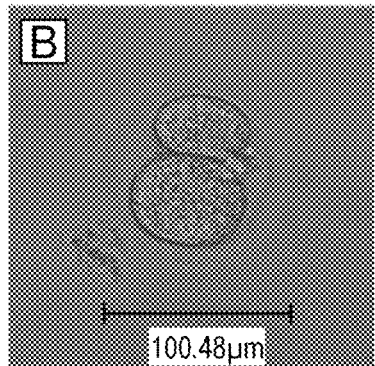
Figure 18:
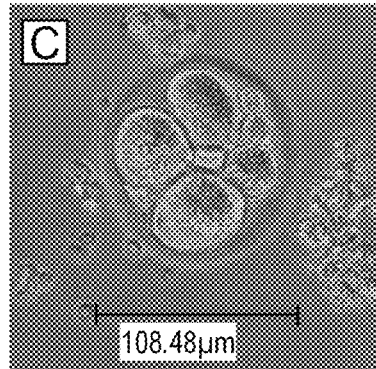

As shown in the images of FIG. 18, the mature oocyte obtained from the bioengineered follicles, when induced with strontium chloride to undergo the parthenogenesis process, divided into a two cell-stage and then into a four cell-stage embryo in vitro, validating their development competency.

The foregoing is illustrative of the present invention, and is not to be construed as limiting thereof. The invention is defined by the following claims, with equivalents of the claims to be included therein.

We claim:
1. An in vitro follicle construct comprising:
 live mammalian oogonia stem cells;
 live mammalian granulosa cells; and
 live mammalian theca cells,
 wherein said oogonia stem cells, said granulosa cells, and/or said theca cells are provided in a hydrogel carrier.
2. The in vitro follicle construct of claim 1, wherein said hydrogel carrier comprises collagen.
3. The in vitro follicle construct of claim 1, wherein:
 said oogonia stem cells are included in the construct in an amount of from 500 cells to 5000 cells;

said granulosa cells are included in the construct in an amount of from 1,000 cells to $1 \times 10^9$ cells; and
 said theca cells are included in said construct in an amount of from 1,000 cells to $1 \times 10^9$ cells.
4. An in vitro method for providing a three-layered bioengineered ovarian follicle, comprising:
 (a) providing a double positive population of cells, wherein said double positive population of cells comprises oogonia stem cells and said double positive population of cells is positive for:
  i) DEAD box helicase peptide 4 (DDX4), and
  ii) interferon-induced transmembrane protein 3 (IFITM3);
 (b) inducing meiosis in the double positive population of cells by exposing them to retinoic acid; then
 (c) adding granulosa cells to the cells and culturing the cells with follicle stimulating hormone (FSH); and then
 (d) adding theca cells and culturing the cells, to thereby provide the three-layered bioengineered ovarian follicle.
5. The method of claim 4, wherein the double positive population of cells comprises human cells.
6. The method of claim 4, wherein the double positive population of cells is produced by:
 (i) providing a mixed population of ovarian cells isolated from an ovary tissue;
 (ii) culture expanding the ovarian cells in a germ-line stem cell medium to form an expanded population; and
 (iii) separating and collecting from the expanded population a population of ovarian cells that are positive for said DDX4 and IFITM3.
7. The method of claim 4, further comprising the step of maturing the ovarian follicle by incubating the follicle in a medium comprising FSH for two to four weeks.
8. The method of claim 7, wherein said method further comprises cyclical incubation of the ovarian follicle with (1) FSH; and (2) a combination of FSH and luteinizing hormone (LH), over period of from 10 or 12 to 16 or 18 days, and then exposing the ovarian follicle to a higher concentration of the LH in a combination of FSH and LH, whereupon an oocyte is released by the ovarian follicle.
9. The method of claim 8, wherein the oocyte released has a diameter of from about 25, 40, or 50 microns to about 70, 90, 100, 110 or 120 microns, or about 70 microns to about 90, 100, 110 or 120 microns.
10. The method of claim 8, wherein the oocyte has cell surface expression of ZP3 and ZP2.
11. The method of claim 8, wherein the oocyte undergoes parthenogenesis upon stimulation with strontium chloride.
12. The in vitro follicle construct of claim 1, wherein one, two, or all three of the live mammalian granulosa cells, live mammalian theca cells, and live mammalian oogonia stem cells are provided by a method comprising:
 (a) separating and collecting from a mixed population of ovarian cells isolated from an ovary tissue, a population of cells that is positive for: i) DEAD box helicase peptide 4 (DDX4), and ii) interferon-induced transmembrane protein 3 (IFITM3), to provide a double positive population of cells, and culturing the double positive population of cells, wherein the double positive population of cells comprises the oogonia stem cells; and/or
 (b) separating and collecting from a mixed population of ovarian cells isolated from an ovary tissue, a population of cells that are not positive for either DDX4 or IFITM3, to provide a population comprising cells that are able to differentiate into granulosa and theca cells, and differentiating the cells of the population into the granulosa and/or theca cells.

13. The in vitro follicle construct of claim 1, wherein the construct is multilayered with the oogonia stem cells in the center, the granulosa cells around the oogonia stem cells as a second layer, and the theca cells around the second layer as a third layer.

* * * * *